United States Patent [19]

Karanewsky et al.

[11] Patent Number: 4,670,422

[45] Date of Patent: Jun. 2, 1987

[54] α-ACYLOXY PHOSPHONATE ANGIOTENSIN CONVERTING ENZYME INHIBITORS

[75] Inventors: Donald S. Karanewsky, East Windsor; Tamara Dejneka, Skillman, both of N.J.

[73] Assignee: E. R. Squibb & Sons, Inc., Princeton, N.J.

[21] Appl. No.: 844,635

[22] Filed: Mar. 27, 1986

[51] Int. Cl.[4] .................. A61K 31/66; A61K 31/675; C07F 9/32; C07F 9/65

[52] U.S. Cl. ........................................ 514/63; 514/79; 514/80; 514/89; 514/92; 514/94; 514/95; 514/99; 514/119; 544/229; 544/337; 546/14; 546/22; 546/23; 548/110; 548/112; 548/119; 548/406; 548/413; 548/414; 548/953; 549/4; 549/6; 549/214; 549/218; 556/19; 558/174

[58] Field of Search .................. 514/63, 79, 80, 89, 514/92, 94, 95, 99, 119; 544/229, 337; 546/14, 22, 23; 548/110, 112, 119, 406, 413, 414, 953; 549/4, 6, 214, 218; 556/19; 558/174

[56] References Cited

U.S. PATENT DOCUMENTS 4,452,790  6/1984  Karanewsky et al. .............. 424/200

Primary Examiner—Richard L. Raymond
Attorney, Agent, or Firm—Lawrence S. Levinson; Stephen B. Davis

[57] ABSTRACT

Compounds of the formula

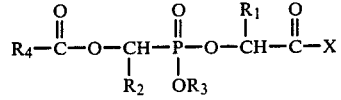

wherein X is various amino or imino acids and esters are disclosed. These compounds are useful as anti-hypertensive agents due to their angiotensin converting enzyme inhibition activity and depending upon the definition of X may also be useful as analgesics due to their enkephalinase inhibition activity.

19 Claims, No Drawings

α-ACYLOXY PHOSPHONATE ANGIOTENSIN CONVERTING ENZYME INHIBITORS

BACKGROUND OF THE INVENTION

Karanewsky et al. in U.S. Pat. No. 4,452,790 disclose angiotensin converting enzyme inhibitors of the formula

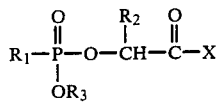

wherein $R_1$ is alkyl, substituted alkylene, or

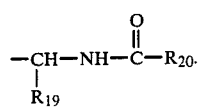

SUMMARY OF THE INVENTION

This invention is directed to new α-acyloxy phosphonate substituted amino or imino acids of formula I and salts thereof

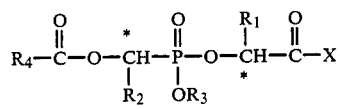 (I)

$R_1$ is hydrogen, lower alkyl, $-(CH_2)_r-Cl$, $-(CH_2)_r-Br$, $-(CH_2)_r-F$, $CF_3$,

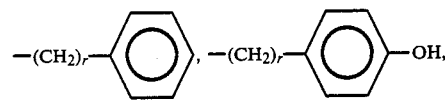

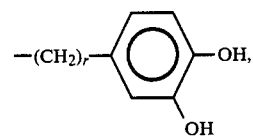

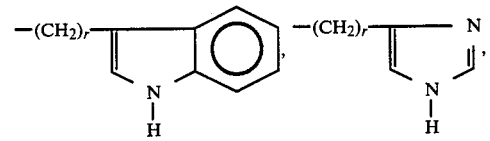

$-(CH_2)_r$-cycloalkyl, $-(CH_2)_r-NH_2$, $-(CH_2)_r-SH$, $-(CH_2)_r-S$-lower alkyl,

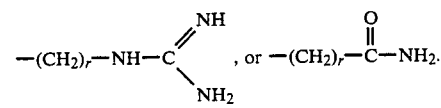

$R_2$ is lower alkyl,

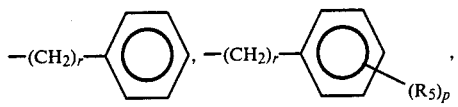

$-(CH_2)_r$-cycloalkyl, or $-(CH_2)_r-NH_2$.

$R_3$ and $R_6$ are independently selected from hydrogen, lower alkyl, benzyl, benzhydryl, alkali metal salt ion, alkaline earth metal salt ion,

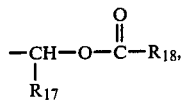

and $-(CH_2)_2-Si(CH_3)_3$.

$R_4$ is straight or branched chain alkyl of 1 to 10 carbons, $-(CH_2)_q$-cycloalkyl,

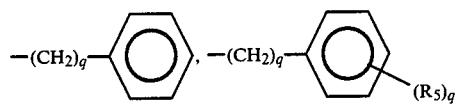

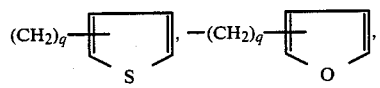

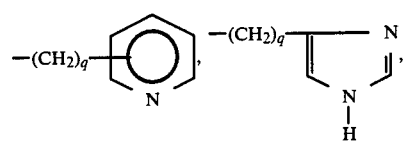

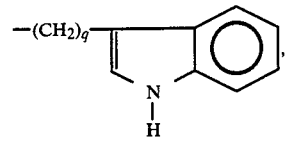

or $-(CH_2)_r-NH_2$.

r is an integer from 1 to 7.
q is zero or an integer from 1 to 7.
X is an amino or imino acid or ester of the formula

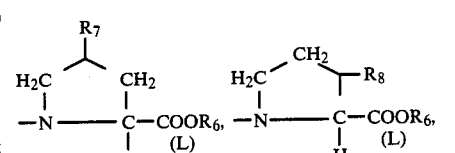

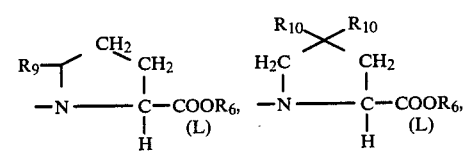

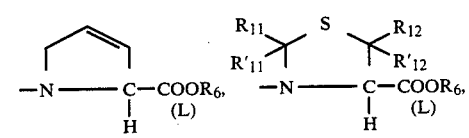

-continued
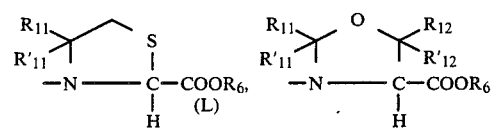 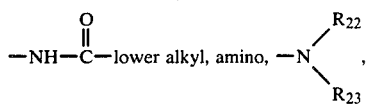
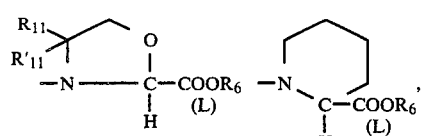 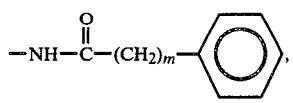
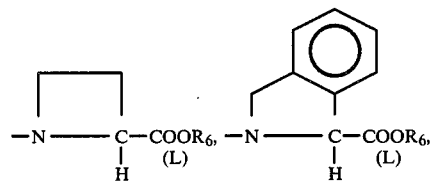 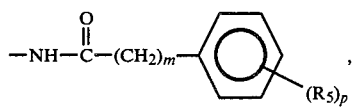
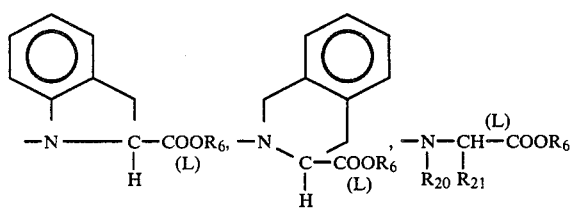 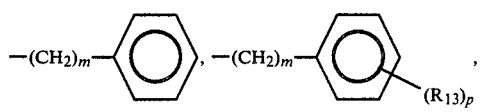
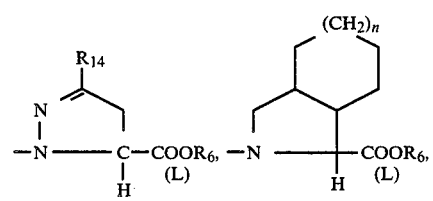 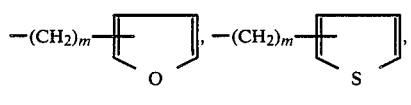
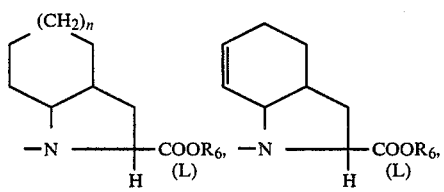 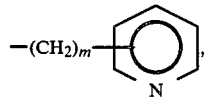
a 1- or 2-naphthyl of the formula
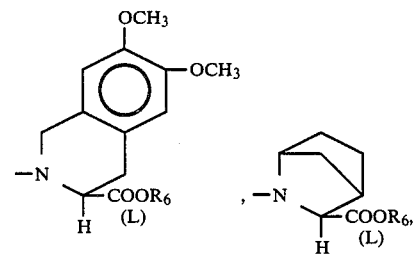 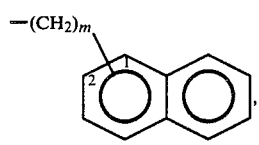
a substituted 1- or 2-naphthyl of the formula
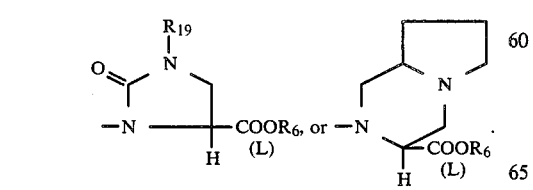 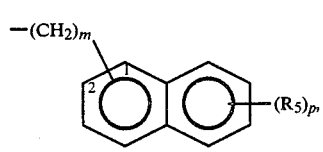
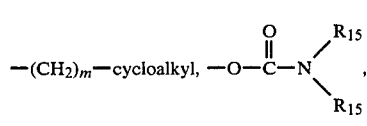
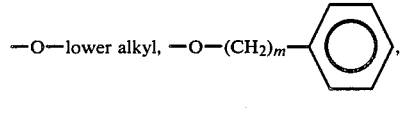
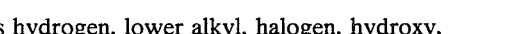
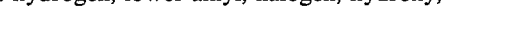
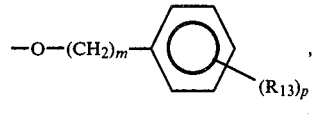
$R_7$ is hydrogen, lower alkyl, halogen, hydroxy,
a 1- or 2- naphthyloxy of the formula

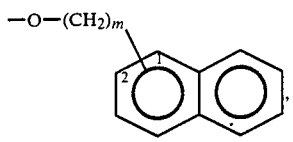

a substituted 1- or 2-naphthyloxy of the formula

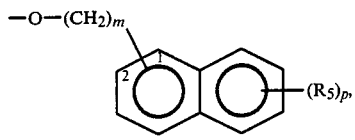

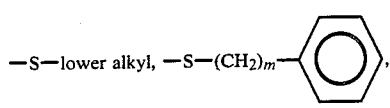

a 1- or 2-naphthylthio of the formula

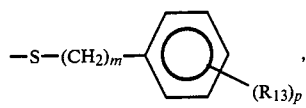

or a substituted 1- or 2-naphthylthio of the formula

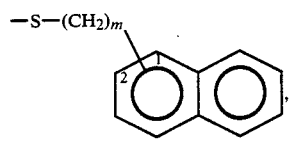

$R_8$ is lower alkyl, halogen,

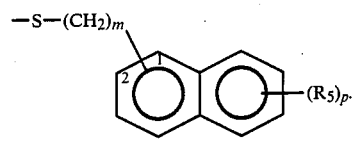

—O-lower alkyl, a 1- or 2-naphthyloxy of the formula

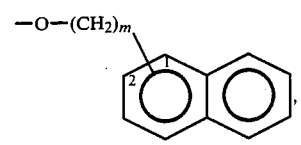

a substituted 1- or 2-naphthyloxy of the formula

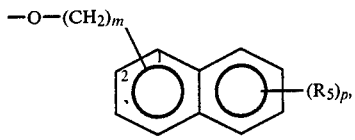

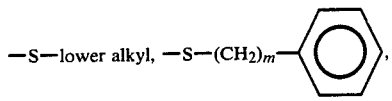

a 1- or 2-naphthylthio of the formula

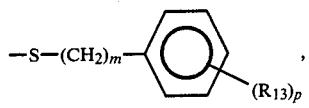

or a substituted 1- or 2-naphthylthio of the formula

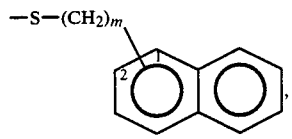

$R_9$ is lower alkyl, keto,

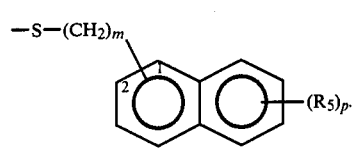

$R_{10}$ is halogen or —Y—$R_{16}$.

$R_{11}$, $R'_{11}$, $R_{12}$ and $R'_{12}$ are independently selected from hydrogen and lower alkyl or $R'_{11}$, $R_{12}$ and $R'_{12}$ are hydrogen and $R_{11}$ is

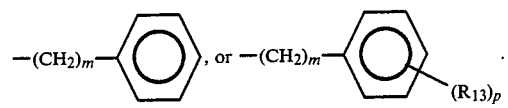

$R_{13}$ is lower alkyl of 1 to 4 carbons, lower alkoxy of 1 to 4 carbons, lower alkylthio of 1 to 4 carbons, chloro, bromo, fluoro, trifluoromethyl, hydroxy, phenyl, phenoxy, phenylthio, or phenylmethyl.

$R_5$ is lower alkyl of 1 to 4 carbons, lower alkoxy of 1 to 4 carbons, lower alkylthio of 1 to 4 carbons, chloro, bromo, fluoro, trifluoromethyl or hydroxy.

m is zero, one, two, three, or four.

p is one, two or three provided that p is more than one only if $R_{13}$ or $R_5$ is methyl, methoxy, chloro, bromo, or fluoro.

$R_{14}$ is hydrogen, lower alkyl,

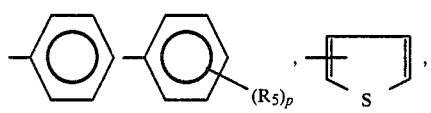

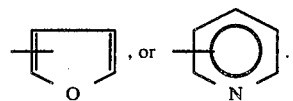

$R_{15}$ is hydrogen or lower alkyl of 1 to 4 carbons.
Y is oxygen or sulfur.
$R_{16}$ is lower alkyl of 1 to 4 carbons,

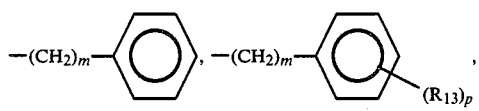

or the $R_{16}$ groups join to complete an unsubstituted 5- or 6-membered ring or said ring in which one or more of the carbons has a lower alkyl of 1 to 4 carbons or a di(lower alkyl of 1 to 4 carbons) substituent.

$R_{17}$ is hydrogen, lower alkyl, cycloalkyl, or phenyl.
$R_{18}$ is hydrogen, lower alkyl, lower alkoxy, or phenyl.
n is zero, one, or two.
$R_{19}$ is lower alkyl or

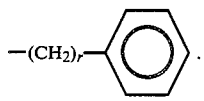

$R_{20}$ is hydrogen, lower alkyl,

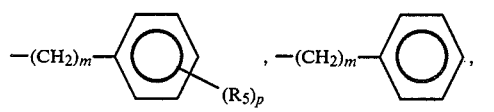

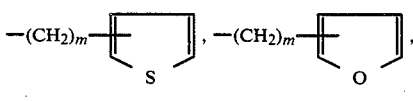

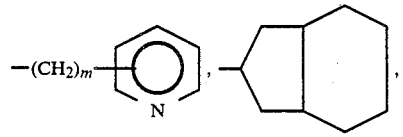

$R_{21}$ is hydrogen, lower alkyl,

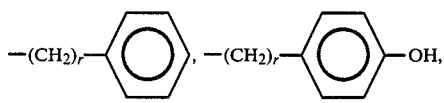

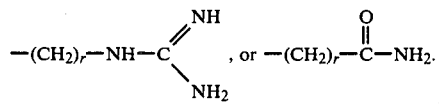

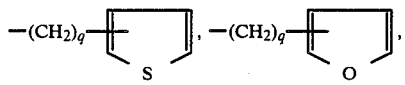

—$(CH_2)_r$—$NH_2$, —$(CH_2)_r$—SH, —$(CH_2)_r$—S-lower alkyl,

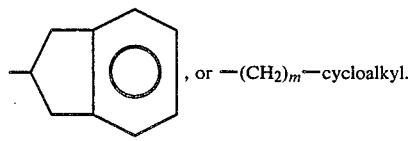

$R_{22}$ is lower alkyl, benzyl, or phenethyl.
$R_{23}$ is hydrogen, lower alkyl, benzyl, or phenethyl.

DETAILED DESCRIPTION OF THE INVENTION

This invention in its broadest aspects relates to the amino and imino acid and ester compounds of formula I and to compositions and the method of using such compounds as pharmaceutical agents.

The term lower alkyl used in defining various symbols refers to straight or branched chain radicals having up to seven carbons. The preferred lower alkyl groups are up to four carbons with methyl and ethyl most preferred. Similarly the terms lower alkoxy and lower alkylthio refer to such lower alkyl groups attached to an oxygen or sulfur.

The term cycloalkyl refers to saturated rings of 4 to 7 carbon atoms with cyclopentyl and cyclohexyl being most preferred.

The term halogen refers to chloro, bromo and fluoro.

The symbols

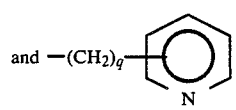

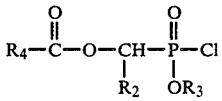

represent that the alkylene bridge is attached to an available carbon atom.

The compounds of formula I can be prepared by coupling a phosphonochloridate of the formula $$\underset{R_2\ \ OR_3}{R_4-\overset{\overset{O}{\|}}{C}-O-\overset{}{C}H-\overset{\overset{O}{\|}}{P}-Cl} \qquad (II)$$

with a hydroxyacyl amino or imino acid ester of the formula

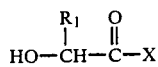 (III)

wherein $R_3$ and $R_6$ (in the definition of X) are easily removable ester protecting groups. For example, preferred ester protecting groups include $R_3$ is methyl and $R_6$ is benzyl. Removal of these ester groups by conventional means, i.e., treatment with trimethylamine when $R_3$ is methyl and hydrogenation in the presence of a palladium catalyst when $R_6$ is benzyl yields the desired products of formula I wherein $R_3$ and $R_6$ are both hydrogen.

The above described coupling reaction is preferably performed in the presence of triethylamine and dimethylaminopyridine.

The phosphonochloridate of formula II can be prepared by reacting an aldehyde of the formula

 (IV)

with a phosphite of the formula

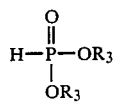 (V)

in the presence of potassium fluoride to give the phosphonic diester of the formula

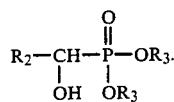 (VI)

Preferably, the dimethyl phosphite is employed, i.e., $R_3$ is methyl.

The diester of formula VI is treated with an acid chloride of the formula

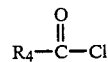 (VII)

in the presence of triethylamine and dimethylaminopyridine to give the phosphonic diester of the formula

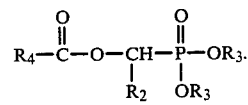 (VIII)

This diester is then treated with a chlorinating agent such as phosphorus pentachloride to give the phosphonochloridate of formula II.

The hydroxyacyl amino or imino acid ester of formula III can be prepared by treating the carboxylic acid of the formula

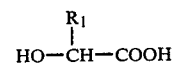 (IX)

with the amino or imino acid ester of the formula

 (X)

wherein $R_6$ in definition of X is an easily removable ester protecting group such as benzyl. Preferably, the hydrochloride salt of the ester of formula X is employed and the reaction is performed in the presence of triethylamine and dicyclohexylcarbodiimide.

In the above reactions if any or all of $R_1$, $R_2$, $R_4$ and $R_{21}$ are

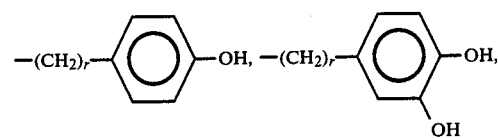

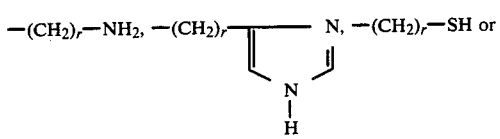

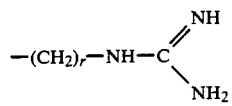

then the hydroxyl, amino, imidazolyl, mercaptan, or guanidinyl function should be protected during the coupling reaction. Suitable protecting groups include benzyloxycarbonyl, t-butoxycarbonyl, benzyl, benzhydryl, trityl, phthalidyl, etc., and nitro in the case of guanidinyl. The protecting group is removed by hydrogenation, treatment with acid, or other known methods following completion of the reaction.

The ester products of formula I wherein $R_6$ is

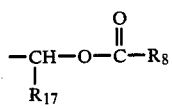

can be obtained by employing the hydroxyacyl amino or imino acid of formula III in the above reactions with the ester group already in place.

The ester products of formula I wherein $R_6$ is

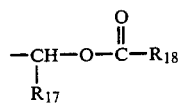

can also be obtained by treating the product of formula I wherein $R_6$ is hydrogen with a molar equivalent of the compound of the formula

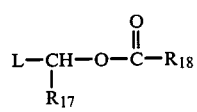 (XI)

wherein L is leaving group such as chlorine, bromine, tolylsulfonyloxy, etc. The diester products wherein $R_3$ and $R_6$ are the same and are both

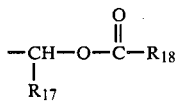

can be obtained by treating the product of formula I wherein $R_3$ and $R_6$ are both hydrogen with two or more equivalents of the compound of formula XI.

The ester products of formula I wherein $R_3$ is

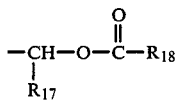

and $R_6$ is hydrogen can be obtained by treating the product of formula I wherein $R_3$ is hydrogen or an alkali metal salt and $R_6$ is benzyl or benzhydryl with the compound of formula XI. Removal of the $R_6$ ester group such as by hydrogenation yields the desired monoester products.

Preferred compounds of this invention with respect to the amino or imino acid part of the structure are those wherein

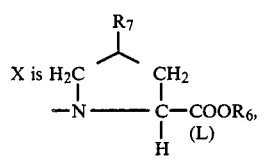

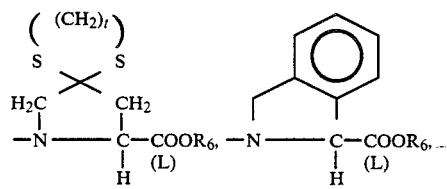

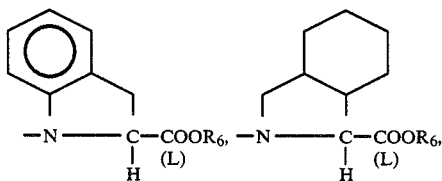

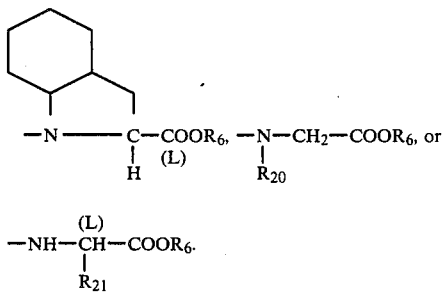

$R_7$ is hydrogen, hydroxy, chloro, fluoro, lower alkyl of 1 to 4 carbons, cyclohexyl, amino, —O-lower alkyl wherein lower alkyl is of 1 to 4 carbons, —S-lower alkyl wherein lower alkyl is of 1 to 4 carbons,

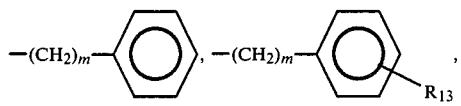

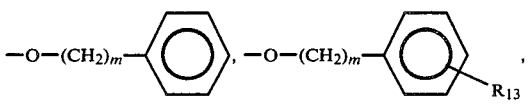

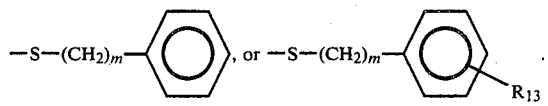

m is zero, one or two.

$R_{13}$ is methyl, methoxy, chloro, fluoro, bromo, methylthio, or hydroxy.

t is 2 or 3.

$R_{21}$ is hydrogen, straight or branched chain lower alkyl of 1 to 4 carbons,

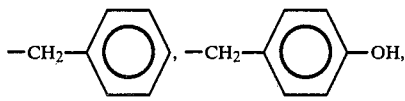

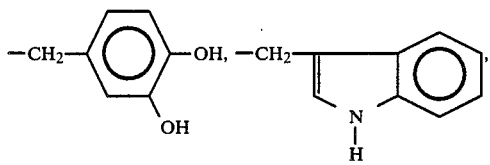

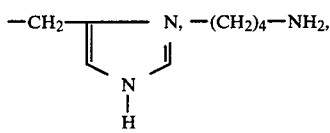

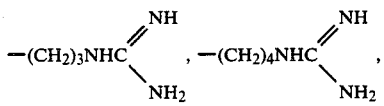

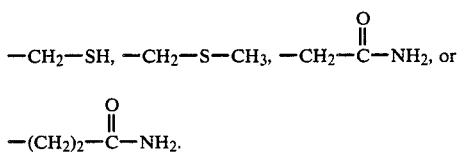

$R_{20}$ is

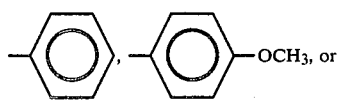

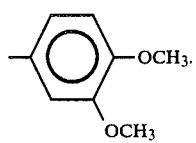

$R_6$ is hydrogen, sodium ion, potassium ion, calcium ion, lithium ion, or $$-\underset{\underset{R_{17}}{|}}{CH}-O-\overset{\overset{O}{\|}}{C}-R_{18}.$$

$R_{17}$ is hydrogen, straight or branched chain lower alkyl of 1 to 4 carbons, cyclohexyl, or phenyl.

$R_{18}$ is hydrogen or straight or branched chain lower alkyl of 1 to 4 carbons.

Most preferred are those wherein:

X is 
$$-\text{N}\underset{\underset{H}{|}}{\overset{\overset{H_2C}{\diagup}\overset{CH_2}{\diagdown}\overset{}{CH_2}}{\diagdown}}\overset{}{\underset{(L)}{C}}-COOR_6.$$

$R_6$ is hydrogen, sodium ion, potassium ion, calcium ion, or lithium ion.

Preferred compounds of this invention with respect to the α-acyloxy phosphonate part of the structures are those wherein:

$R_1$ is straight or branched chain lower alkyl of 1 to 4 carbons, $-(CH_2)_r-NH_2$, or $$-(CH_2)_r-NH-C\underset{\diagdown NH_2}{\overset{\diagup NH}{\|}}$$

wherein r is an integer from 3 to 5.

$R_2$ is straight or branched chain lower alkyl of 1 to 4 carbons, $-CH_2-\bigcirc-(CH_2)_2-\bigcirc$, $-CH_2-\underset{R_5}{\bigcirc}$ or $-(CH_2)_2-\underset{R_5}{\bigcirc}$.

$R_3$ is hydrogen, sodium ion, potassium ion, calcium ion, lithium ion, or $$-\underset{\underset{R_{17}}{|}}{CH}-O-\overset{\overset{O}{\|}}{C}-R_{18}.$$

$R_4$ is straight or branched chain lower alkyl of 1 to 4 carbons, $-(CH_2)_q-\bigcirc$, $-(CH_2)_q-\underset{R_5}{\bigcirc}$, $-(CH_2)_q-\underset{S}{\square}$, $-(CH_2)_q-\underset{O}{\square}$, or $-(CH_2)_q-\underset{N}{\bigcirc}$.

q is zero, one, or two.

$R_5$ is methyl, methoxy, methylthio, chloro, bromo, fluoro, or hydroxy.

$R_{17}$ is hydrogen, straight or branched chain lower alkyl of 1 to 4 carbons, cyclohexyl, or phenyl.

$R_{18}$ is hydrogen or straight or branched chain lower alkyl of 1 to 4 carbons.

Most preferred are those wherein:
$R_1$ is $-(CH_2)_4-NH_2$.
$R_2$ is methyl, n-butyl, or benzyl.
$R_3$ is hydrogen, sodium ion, potassium ion, calcium ion, or lithium ion.
$R_4$ is n-propyl, phenyl, or 2-furanyl.

The compounds of formula I wherein at least one of $R_3$ and $R_6$ is hydrogen form salts with a variety of inorganic or organic bases. The nontoxic, pharmaceutically acceptable salts are preferred, although other salts are also useful in isolating or purifying the product. Such pharmaceutically acceptable salts include alkali metal salts such as sodium, potassium or lithium, alkaline earth metal salts such as calcium or magnesium, and salts derived from amino acids such as arginine, lysine, etc. The salts are obtained by reacting the acid form of the compound with an equivalent of the base supplying the desired ion in a medium in which the salt precipitates or in aqueous medium and then lyophilizing.

As shown above, the amino or imino acid or ester portion of the molecule of the products of formula I as represented by X is in the L-configuration. Also, the products of formula I wherein $R_1$ is other than hydrogen contain two asymmetric centers in the α-acyloxy phosphonate portion of the molecule as represented by the * in formula I. Additional asymmetric centers are present in the ester products when $R_{17}$ is other than hydrogen. Thus, the compounds of formula I can exist in diastereomeric forms or in mixtures thereof. The above described processes can utilize racemates, enantiomers or diastereomers as starting materials. When diastereomeric products are prepared, they can be separated by conventional chromatographic or fractional crystallization methods.

The products of formula I wherein the imino acid ring is monosubstituted give rise to cis-trans isomerism. The configuration of the final product will depend upon the configuration of the $R_7$, $R_8$ and $R_9$ substituent in the starting material of formula III.

The compounds of formula I, and the pharmaceutically acceptable salts thereof, are hypotensive agents. They inhibit the conversion of the decapeptide angiotensin I to angiotensin II and, therefore, are useful in reducing or relieving angiotensin related hypertension. The action of the enzyme renin on angiotensinogen, a pseudoglobulin in blood plasma, produces angiotensin I. Angiotensin I is converted by angiotensin converting enzyme (ACE) to angiotensin II. The latter is an active pressor substance which has been implicated as the causative agent in several forms of hypertension in various mammalian species, e.g., humans. The compounds of this invention intervene in the angiotensinogen→(renin)→angiotensin I→angiotensin II sequence by inhibiting angiotensin converting enzyme and reducing or eliminating the formation of the pressor substance angiotensin II. Thus by the administration of a composition containing one (or a combination) of the compounds of this invention, angiotensin dependent hypertension in a species of mammal (e.g., humans) suffering therefrom is alleviated. A single dose, or preferably two to four divided daily doses, provided on a basis of about 0.1 to 100 mg., preferably about 1 to 50 mg., per kg. of body weight per day is appropriate to reduce blood pressure. The substance is preferably administered orally but parenteral routes such as the subcutaneous, intramuscular, intravenous or intraperitoneal routes can also be employed.

The compounds of this invention can also be formulated in combination with a diuretic for the treatment of hypertension. A combination product comprising a compound of this invention and a diuretic can be administered in an effective amount which comprises a total daily dosage of about 30 to 600 mg., preferably about 30 to 330 mg. of a compound of this invention, and about 15 to 300 mg., preferably about 15 to 200 mg. of the diuretic, to a mammalian species in need thereof. Exemplary of the diuretics contemplated for use in combination of this invention are the thiazide diuretics, e.g., chlorothiazide, hydrochlorothiazide, flumethiazide, hydroflumethiazide, bendroflumethiazide, methyclothiazide, trichloromethiazide, polythiazide or benzthiazide as well as ethacrynic acid, ticrynafen, chlorthalidone, furosemide, musolimine, bumetanide, triamterene, amiloride and spironolactone and salts of such compounds.

The compounds of formula I can be formulated for use in the reduction of blood pressure in compositions such as tablets, capsules or elixirs for oral administration, or in sterile solutions or suspensions for parenteral administration. About 10 to 500 mg. of a compound of formula I is compounded with physiologically acceptable vehicle, carrier, excipient, binder, preservative, stabilizer, flavor, etc., in a unit dosage form as called for by accepted pharmaceutical practice. The amount of active substance in these compositions or preparations is such that a suitable dosage in the range indicated is obtained.

The compounds of formula I wherein X is

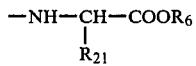

also possess enkephalinase inhibition activity and are useful as analgesic agents. Thus, by the administration of a composition containing one or a combination of such compounds of formula I or a pharmaceutically acceptable salt thereof, pain is alleviated in the mammalian host. A single dose, or preferably two to four divided daily doses, provided on a basis of about 0.1 to about 100 mg. per kilogram of body weight per day, preferably about 1 to about 50 mg. per kilogram per day, produces the desired analgesic activity. The composition is preferably administered orally but parenteral routes such as subcutaneous can also be employed.

The following examples are illustrative of the invention. Temperatures are given in degrees centigrade.

HP-20 refers to a porous crosslinked polystyrene-divinyl benzene polymer resin.

EXAMPLE 1

1-[(S)-6-Amino-2-[[[1-(benzoyloxy)pentyl]hydroxyphosphinyl]oxy]-1-oxohexyl]-L-proline (a) (1-Hydroxypentyl)phosphonic acid, dimethyl ester Valeraldehyde (3.44 g., 0.04 mole), dimethyl phosphite (4.68 g., 0.042 mole), and potassium fluoride (3.8 g., 0.04 mole) are combined and stirred at room temperature for 3 hours under argon. The reaction mixture is diluted with methylene chloride (200 ml.), filtered, and the filtrate is concentrated in vacuo to yield 7.5 g. of (1-hydroxypentyl)phosphonic acid, dimethyl ester as a colorless viscous oil.

(b) [1-(Benzoyloxy)pentyl]phosphonic acid, dimethyl ester

Benzoylchloride (1.4 g., 0.01 mole) and dimethylaminopyridine (1.1 g., 0.01 mole) are added sequentially to a solution of (1-hydroxypentyl)phosphonic acid, dimethyl ester (1.96 g., 0.01 mole) in 20 ml. of 1:1 ether-pyridine. This solution is stored at 10° for 48 hours. It is then diluted with ether (100 ml.) and washed with saturated sodium bicarbonate, water, and brine, dried over sodium sulfate, and concentrated in vacuo to give 2.7 g. of crude product. Flash chromatography (60 g. of LPS-1 silica gel, eluting with 3.5:6.5 hexane:ethyl acetate) gives product containing fractions which are combined and concentrated in vacuo to yield 1.9 g. of [1-(benzoyloxy)pentyl]phosphonic acid, dimethyl ester as a colorless oil.

(c) (S)-6-Amino-2-hydroxyhexanoic acid

An aqueous solution of L-lysine, monohydrochloride (18.3 g., 0.1 mole) is passed through an AG 3-X4A (100–200 mesh) ion exchange column (OH form, 500 ml. bed volume) eluting with water. The ninhydrin positive fractions are combined, acidified with 2M (4N) sulfuric acid (100 ml., 0.2 mole) and evaporated to dryness.

The crude L-lysine, disulfuric acid salt is taken up in 10% sulfuric acid (250 ml.) and treated dropwise with a solution of sodium nitrite (25.9 g., 0.36 mole) in water (100 ml.) at 45°–50° (bath temperature) over a period of 2 hours. When the addition is complete, the mixture is stirred at 45°–50° for an additional 4.5 hours, the excess nitrous acid decomposed with urea and the mixture is poured onto an AG-50-X8 ion exchange column (H+ form, 200 ml. bed volume). The column is eluted with water and then aqueous ammonia (concentrated ammonia-water, 1:3) to elute the product. The ninhydrin positive fractions are combined and evaporated to give a pink semi-solid which is recrystallized from water-ethanol to give 8.20 g. of (S)-6-amino-2-hydroxyhexanoic acid as white crystals; m.p. 197°–199°; $[\alpha]_D^{22} = -12.2°$ (c=1.2, water). TLC(silica gel; isopropanol:concentrated ammonia:water, 7:2:1) $R_f = 0.16$ (contains trace of lysine, $R_f = 0.22$).

(d) (S)-6-[[(Phenylmethoxy)carbonyl]amino]-2-hydroxyhexanoic acid

A solution of (S)-6-amino-2-hydroxyhexanoic acid (7.5 g., 51.0 mmole) in 1N sodium hydroxide solution (50 ml.) at 0° (ice-bath) is adjusted to pH 10.0 with concentrated hydrochloric acid and treated with benzyl chloroformate (8.4 ml., 95%, 55.9 mmole) in approximately 1 ml. portions at 15 minute intervals. Throughout the reaction, the pH is maintained at pH 9.8–10.2 by the addition of 1N sodium hydroxide solution. When the addition is complete and the pH stabilized, the mixture is stirred at pH 10, 0°, for an additional 45 minutes, and then washed with one portion of ethyl ether. The aqueous solution is acidified to pH 1 with concentrated hydrochloric acid and extracted with ethyl acetate. The ethyl acetate extract is washed with saturated sodium chloride solution, dried over sodium sulfate, and evaporated. The residue is crystallized from isopropyl ether to give 13.5 g. of crude product as a white solid. Recrystallization of the crude product from ethyl acetate-hexane gives 11.48 g. of (S)-6-[[(phenylmethoxy)carbonyl]amino]-2-hydroxyhexanoic acid as a white crystalline solid; m.p. 79°–81°; $[\alpha]_D^{22}=+4.5°$, $[\alpha]_{365}=+26.8°$ (c=1.1, chloroform). TLC (silica gel; acetic acid:methanol:methylene chloride, 1:1:20) $R_f=0.19$.

(e)
1-[(S)-6-[[(Phenylmethoxy)carbonyl]amino]-2-hydroxy-1-oxohexyl]-L-proline, phenylmethyl ester A mixture of (S)-6-[[(phenylmethoxy)carbonyl]amino]-2-hydroxyhexanoic acid (1.4 g., 5.0 mmole), L-proline, phenylmethyl ester, monohydrochloride (1.33 g., 5.5 mmole), and triethylamine (0.76 ml., 5.5 mmole) in dry tetrahydrofuran (15 ml.) at 0° (ice-bath) is treated with 1-hydroxybenzotriazole hydrate (0.71 g., 5.26 mmole) and dicyclohexylcarbodiimide (1.08 g., 5.23 mmole). The solution is stirred at 0° for 3 hours, then allowed to warm to room temperature and stirred for an additional one hour. The mixture is filtered, diluted with ethyl acetate, and washed successively with 5% potassium bisulfate, saturated sodium bicarbonate, and saturated sodium chloride, dried over sodium sulfate, and evaporated. The residue is taken up in carbon tetrachloride, filtered to remove the last traces of dicyclohexyl urea, and evaporated. The crude product is purified by flash chromatography on silica gel (35 g., Whatman LPS-1) eluting with ethyl acetate-hexane (2:1) to give 2.24 g. of 1-[(S)-6-[[(phenylmethoxy)carbonyl]amino]-2-hydroxy-1-oxohexyl]-L-proline, phenylmethyl ester as a colorless, very viscous oil. TLC (silica gel; methanol:methylene chloride, 5:95) $R_f=0.36$.

(f)
1-[(S)-2-[[[1-(Benzoyloxy)pentyl]methoxyphosphinyl]oxy]-1-oxo-6-[[(phenylmethoxy)carbonyl]amino]hexyl]L-proline, phenylmethyl ester A solution of [1-(benzoyloxy)pentyl]phosphonic acid, dimethyl ester (1.9 g., 6.3 mmole) in dry benzene (10 ml.) is treated with phosphorus pentachloride (1.4 g., 6.5 mmole) and heated at 70° under argon for 2 hours. The solution is concentrated to dryness and evaporated from benzene.

The resulting crude phosphonochloridate is taken up in dry methylene chloride (2 ml.) and added dropwise to a methylene chloride (8 ml.) solution of 1-[(S)-6-[[(phenylmethoxy)carbonyl]amino]-2-hydroxy-1-oxohexyl]-L-proline, phenylmethyl ester (1.97 g., 4.2 mmole), triethylamine (0.66 g., 6.5 mmole) and dimethylaminopyridine (0.1 g.) at 0° under argon and stirred at 0°–15° for 2 hours. The mixture is partitioned between methylene chloride and 5% potassium bisulfate. The organic phase is washed with brine, dried over magnesium sulfate, and evaporated to dryness. The resulting crude oil is purified by chromatography (LPS-1 silica gel) eluting with (7:3) hexane:acetone. The product containing fractions are combined and concentrated in vacuo to yield 1.55 g. of 1-[(S)-2-[[[1-(benzoyloxy)pentyl]methoxyphosphinyl]oxy-1-oxo-6-[[(phenylmethoxy)carbonyl]amino]hexyl]-L-proline, phenylmethyl ester.

(g)
1-[(S)-2-[[[1-(Benzoyloxy)pentyl]hydroxyphosphinyl]oxy]-1-oxo-6-[[(phenylmethoxy)carbonyl]amino]hexyl]-L-proline, phenylmethyl ester The phenylmethyl ester product from part (f) (1.55 g.) in acetone (8 ml.) is saturated with trimethylamine and heated in a sealed tube at 80° for 16 hours. The reaction mixture is concentrated in vacuo and partitioned between ethyl acetate and 0.1N hydrochloric acid. The organic phase is washed with brine, dried over magnesium sulfate, and concentrated in vacuo to yield 1.43 g. of 1-[(S)-2-[[[1-(benzoyloxy)pentyl]hydroxyphosphinyl]oxy]-1-oxo-6-[[(phenylmethoxy)carbonyl]amino]hexyl]-L-proline, phenylmethyl ester as a viscous colorless oil.

(h)
1-[(S)-6-Amino-2-[[[1-(benzoyloxy)pentyl]hydroxyphosphinyl]oxy]-1-oxohexyl]-L-proline The phenylmethyl ester product from part (g) (1.43 g.) in methanol (30 ml.) is hydrogenated at atmospheric pressure for 20 minutes using 20% palladium hydroxide on carbon catalyst (0.1 g.). The mixture is filtered (Celite) and concentrated to a foam. The crude product is purified on an HP-20 column eluting with 200 ml. portions of water:% acetonitrile (0%, 5%, 10%, 20%, 30%). The product is eluted with 30% acetonitrile:water. The product containing fractions are combined and concentrated in vacuo to 20 ml. and then lyophillized to give 0.8 g. of 1-[(S)-6-amino-2-[[[1-(benzoyloxy)pentyl]-hydroxyphosphinyl]oxy]-1-oxohexyl]-L-proline as a white solid; m.p. 158°–170°; $[\alpha]_D=-40.3°$ (c=0.71, methanol). TLC (silica gel; isopropanol:conc. ammonium hydroxide:water, 7:2:1) $R_f=0.34$.

Anal calc'd. for $C_{23}H_{35}N_2PO_8 \cdot 0.8\ H_2O$:
C, 53.85; H, 7.19; N, 5.46; P, 6.04.
Found: C, 53.82; H, 7.09; N, 5.51; P, 5.80.

EXAMPLE 2

1-[(S)-6-Amino-2-[[[1-(benzoyloxy)ethyl]hydroxyphosphinyl]oxy]-1-oxohexyl]-L-proline (a) (1-Hydroxyethyl)phosphonic acid, dimethyl ester Dimethyl phosphite (5.5 g., 0.05 mole), potassium fluoride (4.7 g., 0.05 mole), and acetaldehyde (2.2 g., 0.05 mole) are stirred overnight under argon. The reaction mixture is diluted with methylene chloride (200 ml.), filtered, and the filtrate is concentrated in vacuo to yield 7.1 g. of (1-hydroxyethyl)phosphonic acid, dimethyl ester.

(b) [1-(Benzoyloxy)ethyl]phosphonic acid, dimethyl ester

Benzoyl chloride (1.4 g., 0.01 mole) and dimethylaminopyridine (1.2 g., 0.01 mmole) are added to a solution of (1-hydroxyethyl)phosphonic acid, dimethyl ester (1.54 g., 0.01 mole) in pyridine. The mixture is stirred for 4 days, diluted with ether (100 ml.), filtered, and the filtrate is washed with 5% potassium bisulfate, saturated sodium bicarbonate, and brine. The ether solution is dried over sodium sulfate, filtered, and concentrated in vacuo to give 1.8 g. of [1-(benzoyloxy)ethyl]phosphonic acid, dimethyl ester. TLC (silica gel; ethyl acetate) $R_f=0.52$.

(c)

1-[(S)-2-[[[1-(Benzoyloxy)ethyl]methoxyphosphinyl]oxy]-1-oxo-6-[[(phenylmethoxy)carbonyl]amino]hexyl]-L-proline, phenylmethyl ester A solution of [1-(benzoyloxy)ethyl]phosphonic acid, dimethyl ester (1.09 g., 4.2 mmole) in dry benzene (10 ml.) is treated with phosphorus pentachloride (0.91 g., 4.4 mmole) and heated at 68°–73° for 3 hours. The solution is concentrated in vacuo and evaporated from benzene (twice).

The resulting crude phosphonochoridate is taken up in dry methylene chloride (2 ml.) and added dropwise to a methylene chloride (5 ml.) solution of 1-[(S)-6-[(phenylmethoxy)carbonyl]amino]-2-hydroxy-1-oxohexyl]-L-proline, phenylmethyl ester (1.4 g., 3 mmole), triethylamine (0.61 ml., 4.4 mmole), and dimethylaminopyridine (0.2 g.) at 5° under argon and stirred for 2 hours. Methylene chloride (200 ml.) is added and the reaction mixture is washed with 5% potassium bisulfate, saturated sodium bicarbonate, and brine. The organic phase is dried over sodium sulfate and concentrated in vacuo. The product is purified by chromatography (100 g., silica gel LPS-1) using a (7:3) hexane:acetone solvent system. The product containing fractions are combined and concentrated in vacuo to yield 1.0 g. of 1-[(S)-2-[[[1-(benzoyloxy)ethyl]methoxyphosphinyl]oxy]-1-oxo-6-[[(phenylmethoxy)carbonyl]amino]hexyl]-L-proline, phenylmethyl ester. TLC (silica gel; ethyl acetate) $R_f=0.47$.

(d)

1-[(S)-2-[[[1-(Benzoyloxy)ethyl]hydroxyphosphinyl]oxy]-1-oxo-6-[[(phenylmethoxy)carbonyl]amino]hexyl]-L-proline, phenylmethyl ester The phenylmethyl ester product from part (c) (1.0 g.) in acetone (10 ml.) is saturated with trimethylamine and heated in a sealed tube at 75°–80° for 16 hours. The reaction mixture is evaporated and the residue is dissolved in ethyl acetate, washed with 1N hydrochloric acid and brine, dried over sodium sulfate, and concentrated in vacuo to yield 0.82 g. of 1-[(S)-2-[[[1-(benzoyloxy)ethyl]hydroxyphosphinyl]oxy-1-oxo-6-[[(phenylmethoxy)carbonyl]amino]hexyl]-L-proline, phenylmethyl ester. TLC (silica gel; methanol:acetic acid:methylene chloride, 1:1:20) $R_f=0.21$.

(e)

1-[(S)-6-Amino-2-[[[1-(benzoyloxy)ethyl]hydroxyphosphinyl]oxy]-1-oxohexyl]-L-proline The phenylmethyl ester product from part (d) (0.82 g.) in methanol (10 ml.) is hydrogenated at atmospheric pressure using 20% palladium hydroxide on carbon catalyst (0.1 g.). The mixture is filtered to remove the catalyst and the filtrate is concentrated in vacuo. The crude reaction mixture is chromatographed on a 75 ml. HP-20 column using a water-acetonitrile solvent system (water, 20% acetonitrile-water, 40% acetonitrile-water). The product containing fractions are combined and lyophillized to give 0.5 g. of 1-[(S)-6-amino-2-[[[1-(benzoyloxy)ethyl]hydroxyphosphinyl]oxy]-1-oxohexyl]-L-proline; m.p. 186°–192°; $[\alpha]_D$ —48.4° (c=0.57, methanol). TLC (silica gel; isopropanol:ammonium hydroxide:water, 7:2:1) $R_f=0.26$.

Anal. calc'd. for $C_{20}H_{24}N_2PO_8 \cdot 0.6\ H_2O$:

C, 51.41; H, 6.52; N, 6.00; P, 6.63.
Found: C, 51.51; H, 6.69; N, 6.05; P, 6.20.

EXAMPLE 3

1-[(S)-6-Amino-2-[[hydroxy[1-(1-oxobutoxy)pentyl]phosphinyl]oxy]-1-oxohexyl]-L-proline, dilithium salt (a) [1-(1-Oxobutoxy)pentyl]phosphonic acid, dimethyl ester Butyryl chloride (1.06 g., 10 mmole) is added to a solution of (1-hydroxypentyl)phosphonic acid, dimethyl ester (1.96 g., 10 mmole) and dimethylaminopyridine (0.1 g.) in pyridine (10 ml.) and the mixture is stirred under argon at room temperature for 48 hours. The reaction mixture is diluted with ether (200 ml.) and washed with saturated sodium bicarbonate, water, and brine, dried over sodium sulfate, and concentrated in vacuo to yield 1.7 g. of [1-(1-oxobutoxy)pentyl]phosphonic acid, dimethyl ester as a colorless oil. TLC (silica gel; ethyl acetate) $R_f=0.67$.

(b)

1-[(S)-2-[[Methoxy[1-(1-oxobutoxy)pentyl]phosphinyl]oxy]-1-oxo-6-[[(phenylmethoxy)carbonyl]amino]hexyl]-L-proline, phenylmethyl ester A solution of [1-(1-oxobutoxy)pentyl]phosphonic acid, dimethyl ester (1.0 g., 4 mmole) in dry benzene (10 ml.) is treated with phosphorus pentachloride (0.9 g., 4.4 mmole) and heated at 70° under argon for 2 hours. The solution is concentrated to dryness and evaporated from benzene.

The resulting crude phosphonochloridate is taken up in dry methylene chloride (2 ml.) and added dropwise to a methylene chloride (8 ml.) solution of 1-[(S)-6-[[(phenylmethoxy)carbonyl]amino]-2-hydroxy-1-oxohexyl]-L-proline, phenylmethyl ester (1.4 g., 3 mmole), triethylamine (0.6 ml., 4.4 mmole), and dimethylaminopyridine (0.2 g.) at 0° under argon and stirred at 0°–15° for 2 hours. The mixture is partitioned between methylene chloride and 5% potassium bisulfate. The organic phase is washed with brine, dried over magnesium sulfate, and evaporated to dryness. The resulting crude product is purified by chromatography (100 g. LPS-1 silica gel) eluting with (7:3) hexane:acetone. The product containing fractions are combined and concentrated in vacuo to yield 1.0 g. of [1-(S)-2-[[methoxy[1-(1-oxobutoxy)pentyl]phosphinyl]oxo]-1-oxo-6-[[(phenylmethoxy)carbonyl]amino]hexyl]-L-proline, phenylmethyl ester as a clear colorless oil.

(c)

1-[(S)-2-[[Hydroxy[1-(1-oxobutoxy)pentyl]phosphinyl]oxy]-1-oxo-6-[[(phenylmethoxy)carbonyl]amino]hexyl]-L-proline, phenylmethyl ester The phenylmethyl ester product from part (b) (1.0 g.) in acetone (8 ml.) is saturated with trimethylamine and heated in a sealed tube at 80° for 16 hours. The reaction mixture is concentrated in vacuo and partitioned between ethyl acetate and 0.1N hydrochloric acid. The organic phase is washed with brine, dried over magnesium sulfate, and concentrated in vacuo to yield 0.88 g. of 1-[(S)-2-[[hydroxy[1-(1-oxobutoxy)pentyl]phosphinyl]oxy]-1-oxo-6-[[(phenylmethoxy)carbonyl]amino]hexyl]-L-proline, phenylmethyl ester.

(d)

1-[(S)-6-Amino-2-[[hydroxy[1-(1-oxobutoxy)pentyl]-phosphinyl]oxy]-1-oxohexyl]-L-proline, dilithium salt The phenylmethyl ester product from part (c) (0.88 g.) in methanol (12 ml.) is hydrogenated at atmospheric pressure for 20 minutes using 20% palladium hydroxide on carbon catalyst (0.2 g.). The mixture is filtered (Celite) and concentrated. The crude product is dissolved in (1:5) acetonitrile:water. 1N Lithium hydroxide is added to pH 9.5 and this material is chromatographed on an HP-20 column eluting with water and 10% acetonitrile:water. The product containing fractions are combined, concentrated, and lyophilized to yield 0.3 g. of 1-[(S)-6-amino-2-[[hydroxy[1-(1-oxobutoxy)pentyl]-phosphinyl]oxy]-1-oxohexyl]-L-proline, dilithium salt as a white solid; m.p. 191°–201° (softens); $[\alpha]_D = -37.6°$ (c=0.5, methanol). TLC (silica gel; isopropanol:conc. ammonium hydroxide:water, 7:2:1) $R_f = 0.25$.

Anal. calc'd. for $C_{20}H_{35}N_2PO_8Li_2$. 1.35 $H_2O$:
C, 47.98; H, 7.59; N, 5.59; P, 6.19.
Found: C, 47.96; H, 7.62; N, 5.48; P, 6.00.

EXAMPLE 4

1-[(S)-6-Amino-2-[[[1-[(2-furanylcarbonyl)oxy]pentyl]-hydroxyphosphinyl]oxy]-1-oxohexyl]-L-proline, dilithium salt (a) [1-[(2-Furanylcarbonyl)oxy]pentyl]phosphonic acid, dimethyl ester Furoyl chloride (0.9, 7 mmole) is added to a solution of (1-hydroxypentyl)phosphonic acid, dimethyl ester (1.3 g., 6.6 mmole) and dimethylaminopyridine in pyridine (8 ml.) and the mixture is stirred under argon at room temperture overnight. The reaction mixture is diluted with ether (100 ml.), filtered, washed with potassium bisulfate (twice), saturated sodium bicarbonate, water, and brine, dried over magnesium sulfate, and concentrated in vacuo to yield 0.75 g. of [1-[(2-furanyl-carbonyl)oxy]pentyl]phosphonic acid, dimethyl ester. TLC (silica gel; ethyl acetate) $R_f = 0.54$.

(b)

1-[(S)-2-[[[1-[(2-Furanylcarbonyl)oxy]pentyl]methoxy-phosphinyl]oxy]-1-oxo-6-[(phenylmethoxy)carbonyl]amino]hexyl]-L-proline, phenylmethyl ester A solution of [1-[(2-furanylcarbonyl)oxy]pentyl]-phosphonic acid, dimethyl ester (0.75 g., 2.6 mmole) in dry benzene (10 ml.) is treated with phosphorus pentachloride (0.58 g., 3.3 mmole) and refluxed for 10 hours and then stored at 0° overnight. The solution is concentrated to dryness and evaporated from benzene.

The resulting crude phosphonochloridate is taken up in dry methylene chloride (2 ml.) and added dropwise to a methylene chloride (8 ml.) solution of 1-[(S)-6-[(phenylmethoxy)carbonyl]amino]-2-hydroxy-1-oxohexyl]-L-proline, phenylmethyl ester (0.94 g., 2 mmole), triethylamine (0.4 ml., 3.3 mmole) and dimethylaminopyridine (0.15 g.) at 0° under argon and stirred at 0°–15° for two hours. The mixture is partitioned between methylene chloride and 5% potassium bisulfate. The organic phase is washed with brine, dried over magnesium sulfate, and evaporated to dryness. The resulting crude product is chromatographed (50 g. of LPS-1 silica gel) eluting with (7:3) hexane:acetone. The product containing fractions are combined and concentrated in vacuo to yield 0.85 g. of 1-[(S)-2-[[[1-[(2-furanylcarbonyl)oxy]pentyl]methoxyphosphinyl-]oxy]-1-oxo-6-[[(phenylmethoxy)carbonyl]amino]hexyl]-L-proline, phenylmethyl ester.

(c)

1-[(S)-2-[[[1-[(2-Furanylcarbonyl)oxy]pentyl]hydroxy-phosphinyl]oxy]-1-oxo-6-[[(phenylmethoxy)carbonyl]amino]hexyl]-L-proline, phenylmethyl ester The phenylmethyl ester product from part (b) (0.85 g.) in acetone (8 ml.) is saturated with trimethylamine and heated in a sealed tube at 80° for 16 hours. The reaction mixture is concentrated in vacuo and partitioned between ethyl acetate and 0.1N hydrochloric acid. The organic phase is washed with brine, dried over magnesium sulfate, and concentrated in vacuo to yield 0.79 g. of 1-[(S)-2-[[[1-[(2-furanylcarbonyl)oxy]pentyl]hydroxyphosphinyl]oxy]-1-oxo-6[[(phenylmethoxy)carbonyl]amino]hexyl]-L-proline, phenylmethyl ester.

(d)

1-[(S)-6-Amino-2-[[[1-[(2-furanylcarbonyl)oxy]pentyl]-hydroxyphosphinyl]oxy]-1-oxohexyl]-L-proline, dilithium salt The phenylmethyl ester product from part (c) (0.79 g.) in methanol (20 ml.) is hydrogenated at atmospheric pressure using 20% palladium hydroxide on carbon catalyst (0.2 g.) for 45 minutes. The mixture is then filtered (Celite), concentrated to a foam, and dissolved in acetonitrile and 1N lithium hydroxide (pH 9.5). The crude product is purified on an HP-20 column eluting with 200 ml. portions of water:% acetonitrile (0%, 10%, 15%, 20%). The product containing fractions are combined, concentrated in vacuo, and lyophillized from water to yield 0.3 g. of 1-[(S)-6-amino-2-[[[1-[(2-furanyl-carbonyl)oxy]pentyl]hydroxyphosphinyl]oxy]-1-oxohexyl]-L-proline, dilithium salt as a white solid; m.p. 200°–207°; $[\alpha]_D = -43.4°$ (c=0.51, methanol). TLC (silica gel; isopropanol:conc. ammonium hydroxide:water, 7:2:1) $R_f = 0.25$.

Anal. calc'd. for $C_{21}H_{31}N_2O_9PLi_2$. 2.75 $H_2O$:
C, 45.87; H, 6.69; N, 5.09; P, 5.63.
Found: C, 45.86; H, 6.66; N, 5.10; P, 5.30.

EXAMPLE 5

1-[(S)-6-Amino-2-[[hydroxy[1-(benzoyloxy)-2-phenyle-thyl]phosphinyl]oxy]-1-oxohexyl]-L-proline, dilithium salt (a) [1-(Hydroxy)-2-phenylethyl]phosphonic acid dimethyl ester Phenylacetaldehyde (6.0 g., 50 mmole), potassium fluoride (4.7 g., 50 mmole), and dimethyl phosphite (5.5 g., 50 mmole) are stirred under argon overnight. The mixture is diluted with methylene chloride, filtered, and concentrated in vacuo. Crystallization from ether yields 5.5 g. of [1-(hydroxy)-2-phenylethyl]phosphonic acid, dimethyl ester; m.p. 83°–86°.

(b) [1-(Benzoyloxy)-2-phenylethyl]phosphonic acid, dimethyl ester

Benzoylchloride (1.4 g., 10 mmole) is added to a solution of [1-(hydroxy)-2-phenylethyl]phosphonic acid, dimethyl ester (2.3 g., 10 mmole) in pyridine (10 ml.) and stirred at room temperature overnight under argon. The mixture is diluted with ether, washed with saturated sodium bicarbonate, water, and brine, dried over magnesium sulfate and concentrated in vacuo to yield 1.8 g. of [1-(benzoyloxy)-2-phenylethyl]phosphonic acid, dimethyl ester. TLC (silica gel; ethyl acetate) $R_f=0.59$.

(c)

1-[(S)-2-[[[1-(Benzoyloxy)-2-phenylethyl]methoxyphosphinyl]oxy]-1-oxo-6-[[(phenylmethoxy)carbonyl]amino]hexyl]-L-proline, phenylmethyl ester A solution of [1-(benzoyloxy)-2-phenylethyl]phosphonic acid, dimethyl ester (1.34 g., 4 mmole) in dry benzene (10 ml.) is treated with phosphorus pentachloride (0.91 g., 4.4 mmole) and heated at reflux under argon for 2 hours. The solution is concentrated to dryness and evaporated from benzene.

The resulting crude phosphonochloridate is taken up in dry methylene chloride (2 ml.) and added dropwise to a methylene chloride (9 ml.) solution of 1-[(S)-6-[[(phenylmethoxy)carbonyl]amino]-2-hydroxy-1-oxohexyl]-L-proline, phenylmethyl ester (1.41 g., 3 mmole), triethylamine (0.62 ml., 4.4 mmole), and dimethylaminopyridine (0.2 g.) at 0° under argon and stirred at 0°–15° for 2 hours. The mixture is partitioned between methylene chloride and 5% potassium bisulfate. The organic phase is washed with brine, dried over magnesium sulfate, and evaporated to dryness. The resulting crude product is selectively filtered through a pad of silica gel (SiliCar CC-7) using ethyl acetate:hexane (1:1). The filtrate is evaporated to yield 1.3 g. of 1-[(S)-2-[[[1-(benzoyloxy)-2-phenylethyl]methoxyphosphinyl]oxy]-1-oxo-6-[[(phenylmethoxy)carbonyl]amino]hexyl]-L-proline, phenylmethyl ester.

(d)

1-[(S)-2-[[[1-(Benzoyloxy)-2-phenylethyl]hydroxyphosphinyl]oxy]-1-oxo-6-[[(phenylmethoxy)carbonyl]amino]hexyl]-L-proline, phenylmethyl ester The phenylmethyl ester product from part (c) (1.3 g.) is dissolved in acetone (10 ml.) saturated with trimethylamine and heated in a sealed tube at 74° for 16 hours. The solution is evaporated and the residue is partitioned between ethyl acetate and 1N hydrochloric acid. The organic phase is washed with brine, dried over sodium sulfate, and concentrated in vacuo to give 1.2 g. of 1-[(S)-2-[[[1-(benzoyloxy)-2-phenylethyl]hydroxyphosphinyl]oxy]-1-oxo-6-[[(phenylmethoxy)carbonyl]amino]hexyl]-L-proline, phenylmethyl ester.

(e)

1-[(S)-6-Amino-2-[[hydroxy[1-(benzoyloxy)-2-phenylethyl]phosphinyl]oxy]-1-oxohexyl]-L-proline, dilithium salt The phenylmethyl ester product from part (d) (1.2 g.) in methanol (10 ml.) is hydrogenated at atmospheric pressure using 20% palladium hydroxide on carbon catalyst (0.3 g.) for 40 minutes. The mixture is filtered (Celite), concentrated to a foam, and dissolved in acetonitrile and 1N lithium hydroxide at pH 9.5. The crude product is purified on an HP-20 column (75 ml.) eluting with 300 ml. portions of water:% acetonitrile (0%, 5%, 15%). The product containing fractions are combined, concentrated in vacuo, and lyophillized from water to give 0.33 g. of 1-[(S)-6-amino-2-[[hydroxy[1-(benzoyloxy)-2-phenylethyl]phosphinyl]oxy]-1-oxohexyl]-L-proline, dilithium salt as a white solid; m.p. 210°–218°; $[\alpha]_D = -11.2°$ (c=0.5, methanol). TLC (silica gel; isopropanol:conc. ammonium hydroxide:water, 7:2:1) $R_f=0.32$.

Anal. calc'd. for $C_{26}H_{31}N_2O_8PLi_2 \cdot 2.2\ H_2O$:
C, 53.47; H, 6.11; N, 4.80; P, 5.30.
Found: C, 53.44; H, 6.26; N, 4.81; P, 5.15.

EXAMPLES 6–40

Following the procedure of Examples 1 to 5, the phosphonochloridate shown below in Col. I is coupled to the hydroxyacyl amino or imino acid ester shown below in Col. II to give the ester product shown below in Col. III. Removal of the $R_3$ and $R_6$ ester protecting groups yields the corresponding diacid shown in Col. IV. In the case of Examples 38 to 40, only the $R_3$ ester group is removed.

| | Col. I | Col. II | | | Col. III | | Col. IV | |
|---|---|---|---|---|---|---|---|---|
| | $R_4-\overset{O}{\overset{\|}{C}}-O-\overset{R_2}{\overset{\|}{CH}}-\overset{O}{\overset{\|}{P}}-Cl$ <br> $OR_3$ | $\overset{R_1}{\overset{\|}{HO-CH}}-\overset{O}{\overset{\|}{C}}-X$ | | | $R_4-\overset{O}{\overset{\|}{C}}-O-\overset{R_2}{\overset{\|}{CH}}-\overset{O}{\overset{\|}{P}}-O-\overset{R_1}{\overset{\|}{CH}}-\overset{O}{\overset{\|}{C}}-X$ <br> $OR_3$ | | $R_4-\overset{O}{\overset{\|}{C}}-O-\overset{R_2}{\overset{\|}{CH}}-\overset{O}{\overset{\|}{P}}-O-\overset{R_1}{\overset{\|}{CH}}-\overset{O}{\overset{\|}{C}}-X$ <br> $OH$ | |
| Example | $R_4$ | $R_3$ | $R_2$ | | $R_1$ | X | | X |
| 6 | thiophene-CH₂- | —CH₃ | —CH₂-Ph | | —H | | | 4-methoxy-benzyl-COOCH₂Ph (L) |
| 7 | pyridine-CH₂- | —CH₃ | —CH₂-Ph | | —CH₃ | | | phenoxymethyl-COOCH₂Ph (L) |
| 8 | indole-CH₂- | —CH₃ | —CH₂-Ph | | —CH₂-Ph | | | fluoro-COOCH₂Ph (L) |
| 9 | indole-CH₂- | —CH₃ | —CH₂-Ph | | —(CH₂)₄NH-C(O)-O-CH₂-Ph | | | cyclohexyl-COOCH₂Ph (L) |

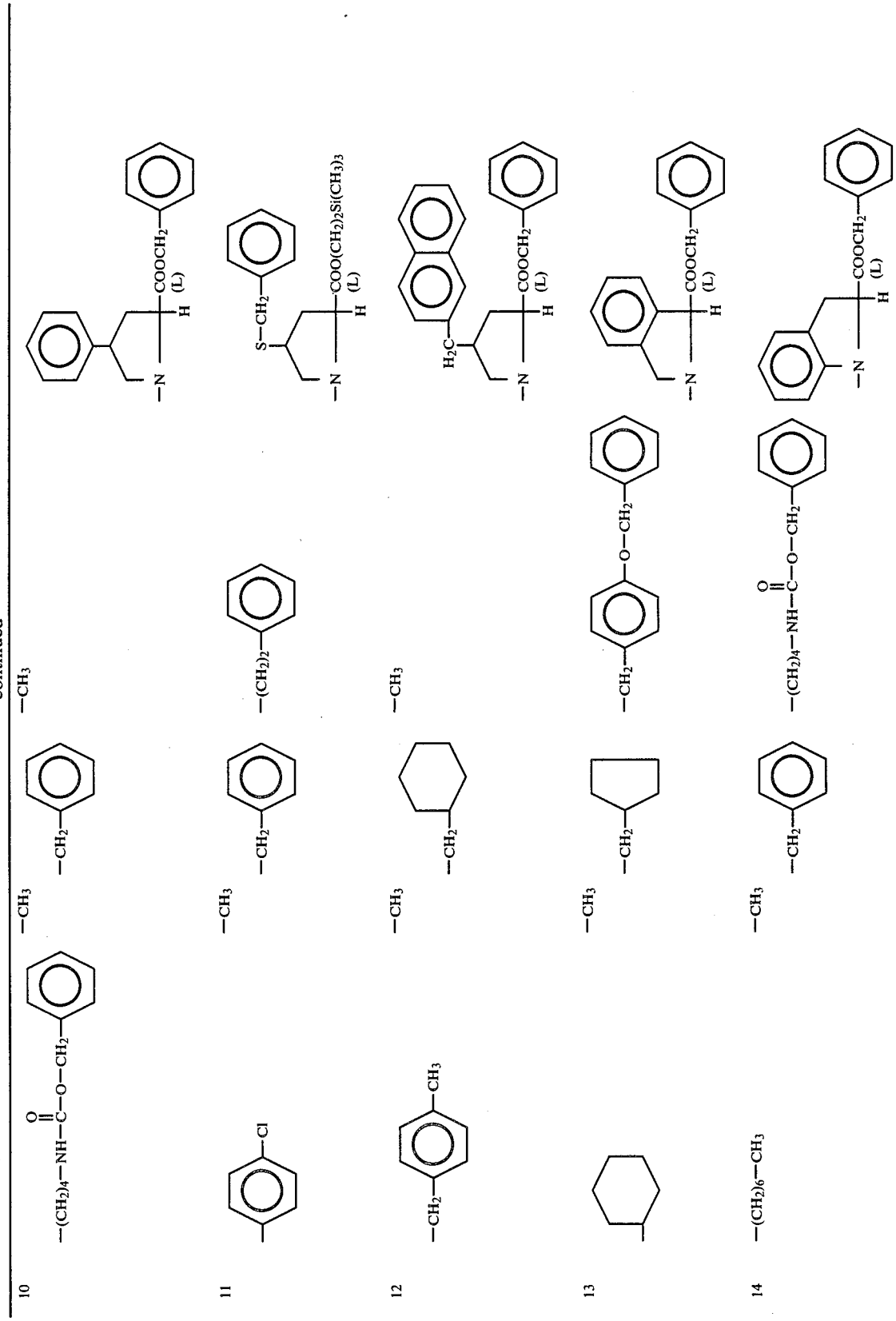

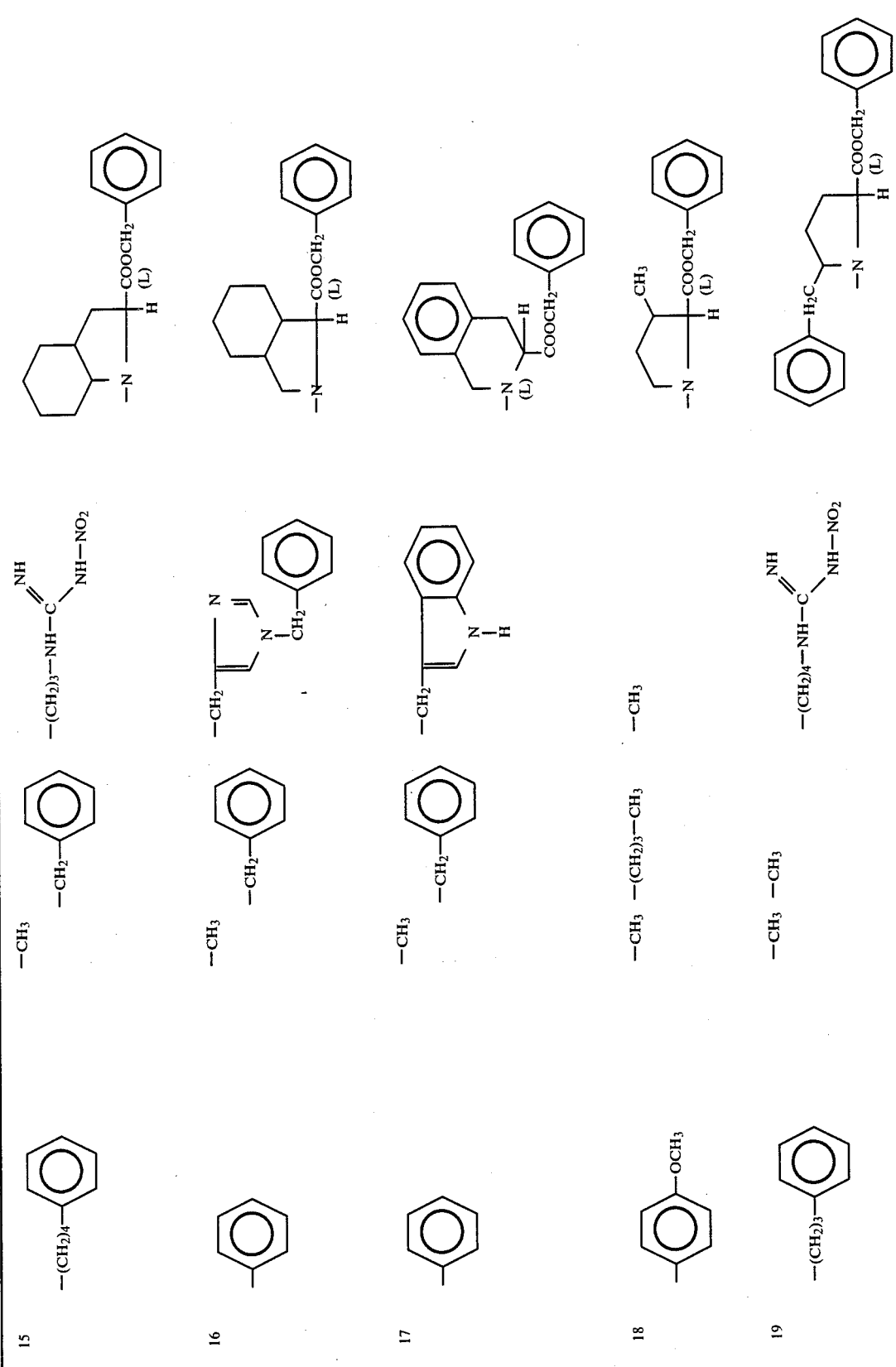

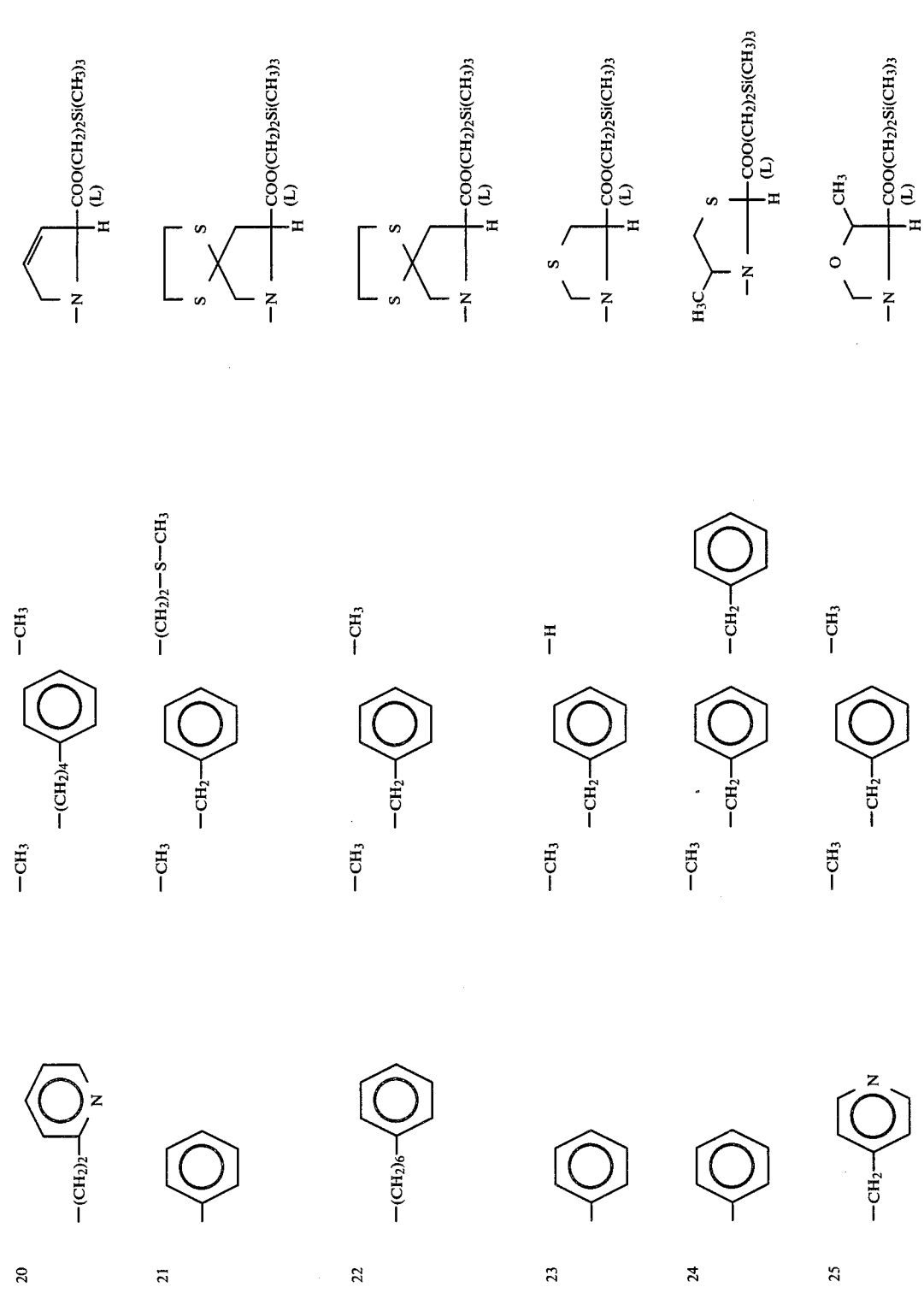

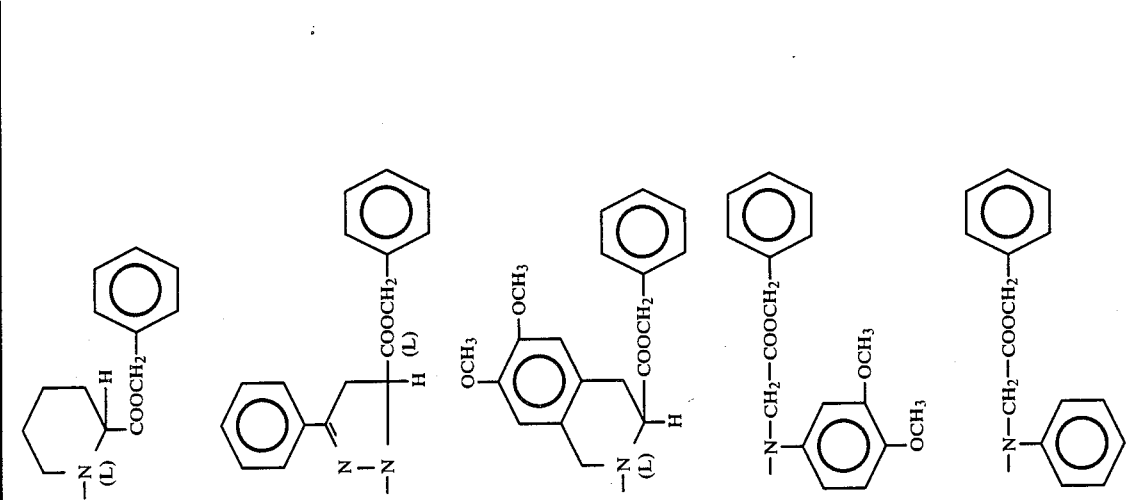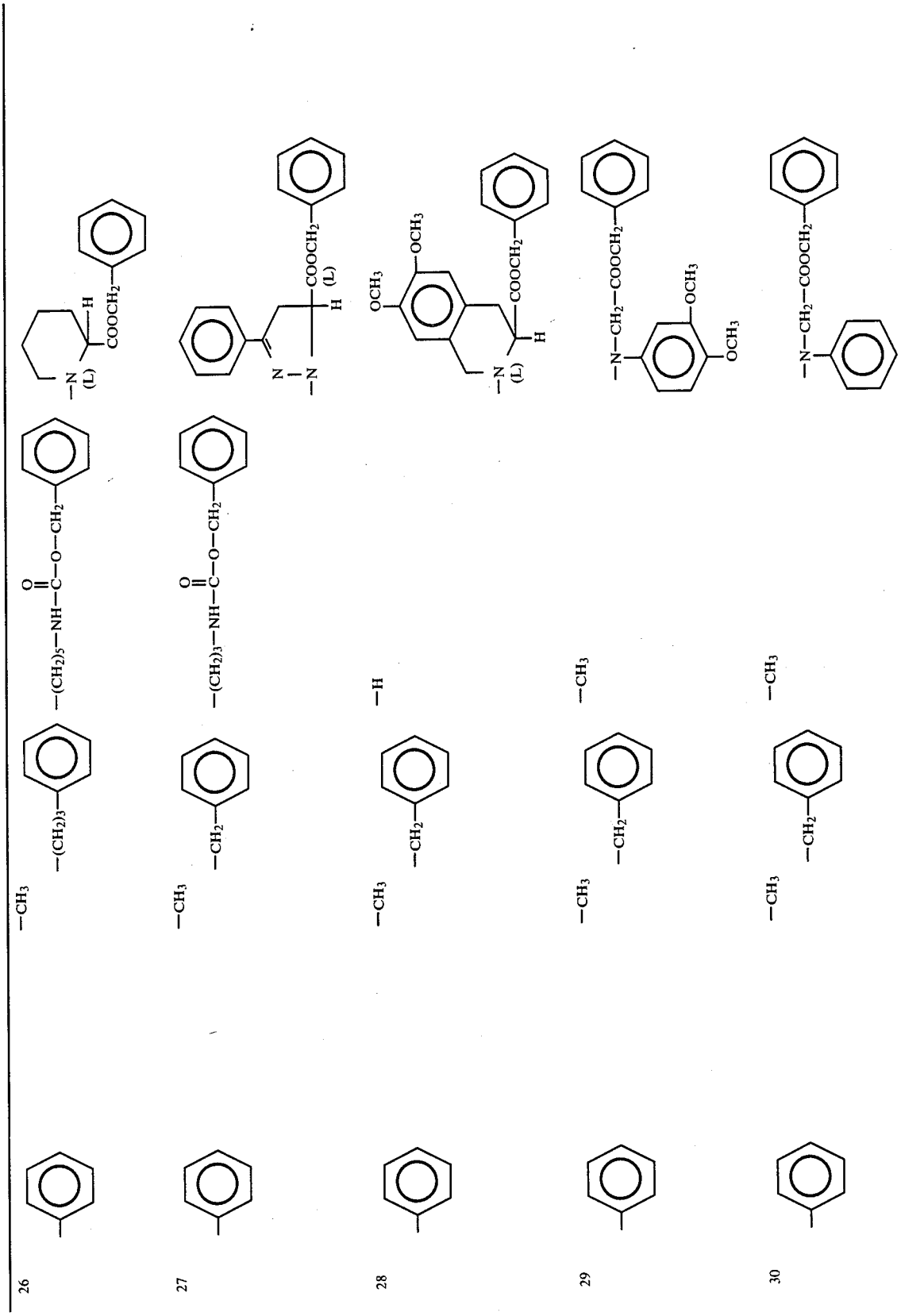

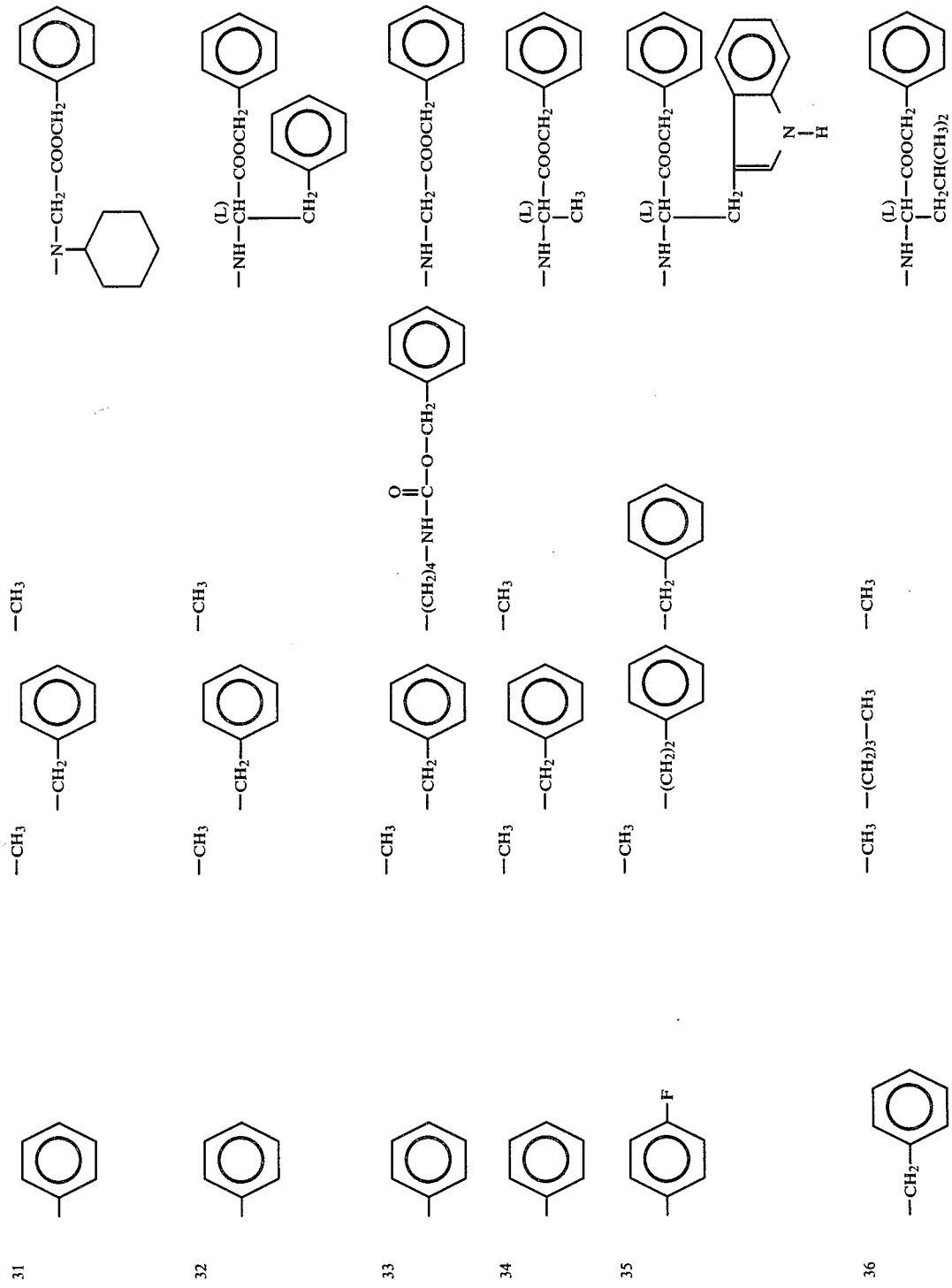

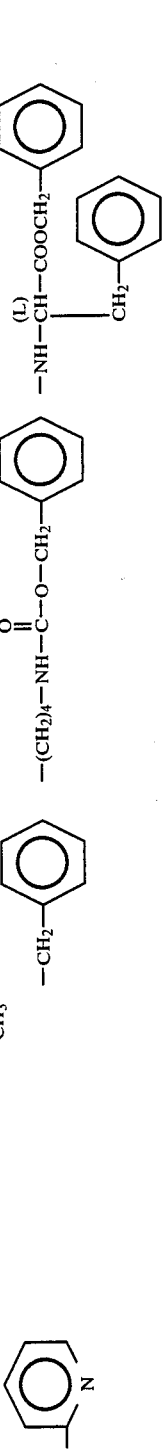

The R₁ protecting groups shown in Examples 9, 13 to 16, 19, 26, 27, 33, and 37 to 39 and the R₄ protecting groups shown in Examples 8 and 10 are removed as the last step in the synthesis.

EXAMPLE 41

1-[(S)-6-Amino-2-[[[(2,2-dimethyl-1-oxopropoxy)methoxy][1-(benzoyloxy)-2-phenylethyl]phosphinyl]oxy]-1-oxohexyl]-L-proline, monolithium salt (a)

1-[(S)-2-[[[(2,2-Dimethyl-1-oxopropoxy)methoxy][1-(benzoyloxy)-2-phenylethyl]phosphinyl]oxy]-1-oxo-6-[[(phenylmethoxy)carbonyl]amino]hexyl]-L-proline, phenylmethyl ester 1-[(S)-2-[[[1-(Benzoyloxy)-2-phenylethyl]hydroxyphosphinyl]oxy]-1-oxo-6-[[(phenylmethyoxy)carbonyl]amino]hexyl]-L-proline,phenylmethyl ester from Example 5(d) is suspended in dry dimethylformamide and treated with chloromethylpivalate. After several hours, additional chloromethylpivalate and anhydrous potassium carbonate are added and the resulting mixture is stirred overnight. The mixture is then diluted with ethyl acetate and washed successively with water, 5% potassium bisulfate, saturated sodium bicarbonate, and saturated sodium chloride solution, dried (Na₂SO₄), and evaporated. The residue is purified by flash chromatography (silica gel) to give 1-[(S)-2-[[[(2,2-dimethyl-1-oxopropoxy)methoxy][1-(benzoyloxy)-2-phenylethyl]phosphinyl]oxy]-1-oxo]-6-[[(phenylmethoxy)carbonyl]amino]hexyl]-L-proline, phenylmethyl ester.

(b)

1-[(S)-6-Amino-2-[[[(2,2-dimethyl-1-oxopropoxy)methoxy][1-(benzoyloxy)-2-phenylethyl]phosphinyl]oxy]-1-oxohexyl]-L-proline, monolithium salt.

The phenylmethyl ester product from part (a) is hydrogenated using 20% palladium hydroxide on carbon catalyst and the residue is treated with 1N lithium hydroxide according to the procedure of Example 5(e) to give 1-[(S)-6-amino-2-[[[(2,2-dimethyl-1-oxopropoxy)methoxy][1-(benzoyloxy)-2-phenylethyl]phosphinyl]oxy]-1-oxohexyl]-L-proline, monolithium salt.

EXAMPLES 42–45

Following the procedure of 41 but substituting for the chloromethylpivalate the alkylating agents listed below in Col. I, the products listed below in Col. II are obtained.

| Example | Col. I | Col. II |
|---|---|---|
| 42 | Cl—CH(cyclohexyl)—O—C(=O)—C₂H₅ | 1-[(S)—6-Amino-2-[[[Cyclohexyl(1-oxopropoxy)methoxy][1-benzoyloxy)-2-phenylethyl]phosphinyl]oxy]-1-oxohexyl]-L-proline, monolithium salt |
| 43 | Cl—CH(CH(CH₃)₂)—O—C(=O)—C₂H₅ | 1-[(S)—6-Amino-2-[[[2-methyl-1-(oxopropoxy)-propoxy][1-(benzoyloxy)-2-phenylethyl]phosphinyl]oxy]-1-oxohexyl]-L-proline, monolithium salt |
| 44 | Cl—CH(CH(CH₃)₂)—O—C(=O)—(CH₂)₃CH₃ | 1-[(S)—6-Amino-2-[[[2-methyl-1-[(1-oxopentyl)oxy]propoxy][1-(benzoyloxy)-2-phenylethyl]phosphinyl]oxy]-1-oxohexyl]-L-proline, monolithium salt |
| 45 | Cl—CH₂—O—C(=O)—phenyl | 1-[(S)—6-Amino-2-[[[(benzoyloxy)methoxy]-[1-(benzoyloxy)-2-phenylethyl]phosphinyl]oxy]-1-oxohexyl]-L-proline, monolithium salt |

Similarly, the alkylating agents of Examples 41 to 45 can be employed with the ester products of Examples 1 to 4 and 6 to 37 to yield other compounds within the scope of this invention.

EXAMPLE 46

1000 tablets each containing the following ingredients

| | |
|---|---|
| 1-[(S)—6-Amino-2-[[hydroxy-[1-(benzoyloxy)-2-phenylethyl]phosphinyl]oxy]-1-oxohexyl]-L-proline, dilithium salt | 100 mg. |
| Cornstarch | 50 mg. |
| Gelatin | 7.5 mg. |
| Avicel (Microcrystalline cellulose) | 25 mg. |
| Magnesium stearate | 2.5 mg. |
| | 185 mg. | are prepared from sufficient bulk quantities by mixing the 1-[(S)-6-amino-2-[[hydroxy[1-(benzoyloxy)-2-phenylethyl]phosphinyl]oxy]-1-oxohexyl]-L-proline, dilithium salt and cornstarch with an aqueous solution of the gelatin. The mixture is dried and ground to a powder. The Avicel and then the magnesium stearate are admixed with granulation. This mixture is then compressed in a tablet press to form 1000 tablets each containing 100 mg. of active ingredient. This same procedure can be employed to prepare tablets containing 50 mg. of active ingredient.

Similarly, tablets containing 100 mg. of the product of any of Examples 1 to 4 and 6 to 45 can be prepared.

EXAMPLE 47

Two piece #1 gelatin capsules are filled with a mixture of the following ingredients:

| | |
|---|---|
| 1-[(S)—6-Amino-2-[[[1-(benzoyloxy)pentyl]-hydroxyphosphinyl]oxy]-1-oxohexyl]-L-proline | 100 mg. |
| Magnesium stearate | 7 mg. |
| Lactose | 193 mg. |
| | 300 mg. |

In a similar manner, capsules containing 100 mg. of the product of any of Examples 2 to 45 can be prepared.

EXAMPLE 48

An injectable solution is prepared as follows:

| | |
|---|---|
| 1-[(S)—6-Amino-2-[[[1-[(2-furanylcarbonyl)oxy]pentyl]-hydroxyphosphinyl]oxy]-1-oxo-hexyl]-L-proline, dilithium salt | 500 g. |
| Methyl paraben | 5 g. |
| Propyl paraben | 1 g. |
| Sodium chloride | 25 g. |
| Water for injection | 5 l. |

The active substance, preservatives, and sodium chloride are dissolved in 3 liters of water for injection and then the volume is brought up to 5 liters. The solution is filtered through a sterile filter and aseptically filled into presterilized vials which are closed with presterilized rubber closures. Each vial contains 5 ml. of solution in a concentration of 100 mg. of active ingredient per ml. of solution for injection.

In a similar manner, an injectable solution containing 100 mg. of active ingredient per ml. of solution can be prepared for the product of any of Examples 1 to 3 and 5 to 45.

EXAMPLE 49

1000 tablets each containing the following ingredients:

| | |
|---|---|
| 1-[(S)—6-Amino-2-[[hydroxy-[1-(benzoyloxy-2-phenylethyl]-phosphinyl]oxy]-1-oxohexyl]-L-proline, dilithium salt | 100 mg. |
| Avicel | 100 mg. |
| Hydrochlorothiazide | 12.5 mg. |
| Lactose | 113 mg. |
| Cornstarch | 17.5 mg. |
| Stearic acid | 7 mg. |
| | 350 mg. | are prepared from sufficient bulk quantities by slugging the 1-[(S)-6-amino-2-[[hydroxy[1-(benzoyloxy)-2-phenylethyl]phosphinyl]oxy]-1-oxohexyl]-L-proline, dilithium salt, Avicel, and a portion of the stearic acid. The slugs are ground and passed through a #2 screen, then mixed with the hydrochlorothiazide, lactose, cornstarch, and the remainder of the stearic acid. The mixture is compressed into 350 mg. capsule shaped tablets in a tablet press. The tablets are scored for dividing in half.

In a similar manner, tablets can be prepared containing 100 mg. of the products of any of Examples 1 to 4 and 6 to 45.

What is claimed is:

1. A compound of the formula $$R_4-\overset{O}{\underset{\|}{C}}-O-\underset{\underset{R_2}{|}}{CH}-\overset{O}{\underset{\|}{P}}-O-\underset{\underset{OR_3}{|}}{CH}-\overset{R_1}{\underset{|}{C}}\overset{O}{\underset{\|}{}}-X$$

including a pharmaceutically acceptable salt thereof wherein:

$R_1$ is hydrogen, lower alkyl, $-(CH_2)_r-Cl$, $-(CH_2)_r-Br$, $-(CH_2)_r-F$, $-CF_3$, $-(CH_2)_r-\bigcirc$, $-(CH_2)_r-\bigcirc-OH$, $-(CH_2)_r-\bigcirc-OH$ (with OH), $-(CH_2)_r-\bigcirc$ (indole), $-(CH_2)_r-\bigcirc$ (imidazole-like), $-(CH_2)_r$-cycloalkyl, $-(CH_2)_r-NH_2$, $-(CH_2)_r-SH$, $-(CH_2)_r-S$-lower alkyl, $-(CH_2)_r-NH-\underset{NH_2}{\overset{NH}{C}}$, or $-(CH_2)_r-\overset{O}{\underset{\|}{C}}-NH_2$;

$R_2$ is lower alkyl, $-(CH_2)_r-\bigcirc$, $-(CH_2)_r-\bigcirc(R_5)_p$, $-(CH_2)_r$-cycloalkyl, or $-(CH_2)_r-NH_2$;

$R_3$ and $R_6$ are independently selected from hydrogen, lower alkyl, benzyl, benzhydryl, alkali metal salt ion, alkaline earth metal salt ion, $-\underset{\underset{R_{17}}{|}}{CH}-O-\overset{O}{\underset{\|}{C}}-R_{18}$ and $-(CH_2)_2Si(CH_3)_3$;

$R_4$ is straight or branched chain alkyl of 1 to 10 carbons, $-(CH_2)_q$-cycloalkyl, $-(CH_2)_q-\bigcirc$, $-(CH_2)_q-\bigcirc(R_5)_q$, $-(CH_2)_q-\bigcirc_S$, $-(CH_2)_q-\bigcirc_O$, $-(CH_2)_q-\bigcirc_N$, $-(CH_2)_q-\bigcirc$ (imidazole-like), $-(CH_2)_q-\bigcirc$ (indole), or —(CH$_2$)$_r$—NH$_2$;
r is an integer from 1 to 7;
q is zero or an integer from 1 to 7;
X is an amino or imino acid or ester of the formula
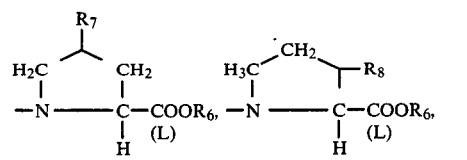
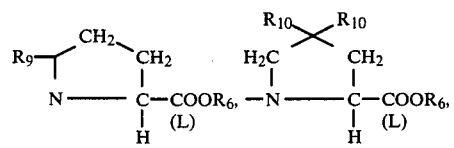
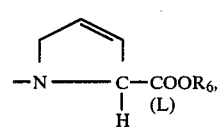
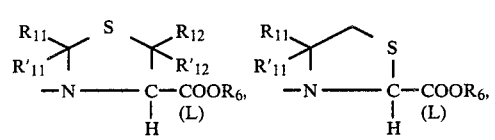
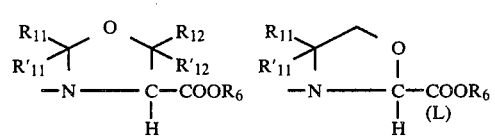
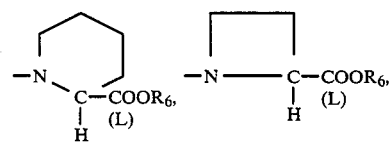
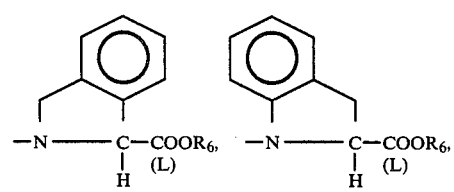
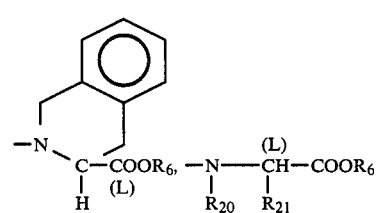
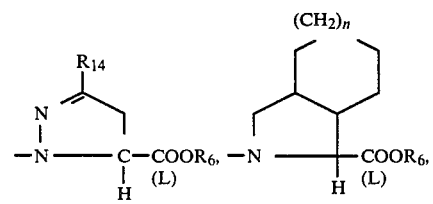
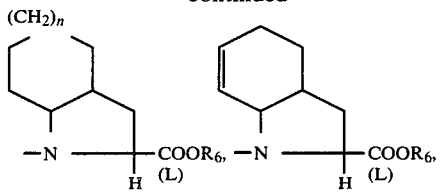
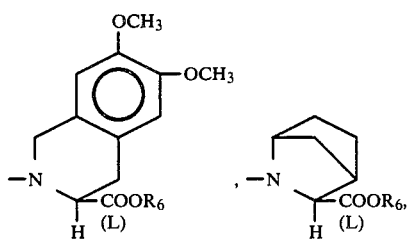
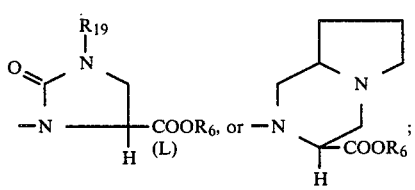
$R_7$ is hydrogen, lower alkyl, halogen, hydroxy,
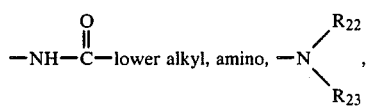
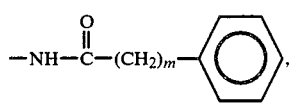
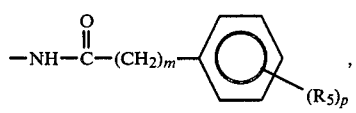
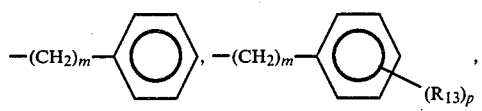
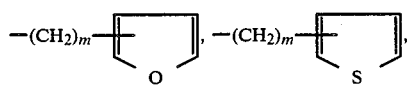
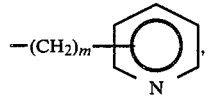
a 1- or 2-naphthyl of the formula
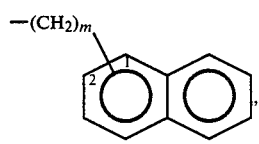
a substituted 1- or 2-naphthyl of the formula

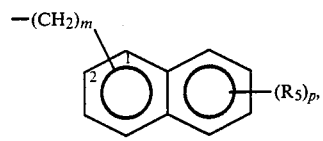

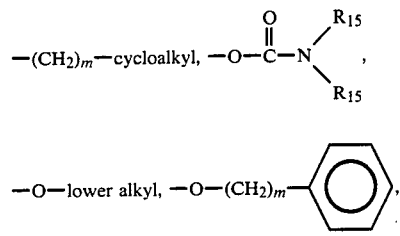

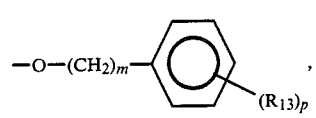

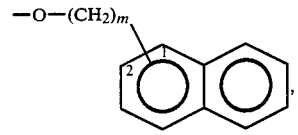

a 1- or 2- naphthyloxy of the formula

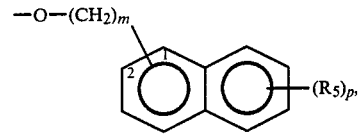

a substituted 1- or 2-naphthyloxy of the formula

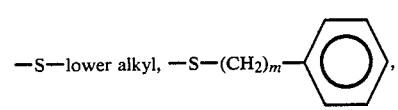

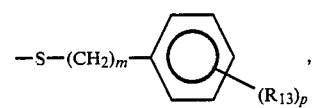

1- or 2-naphthylthio of the formula

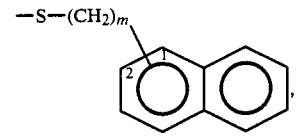

or a substituted 1- or 2-naphthylthio of the formula

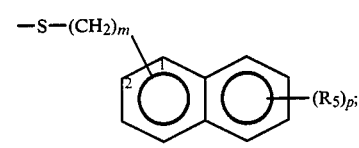

$R_8$ is lower alkyl, halogen,

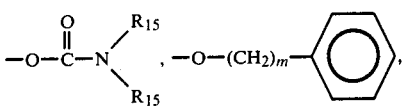

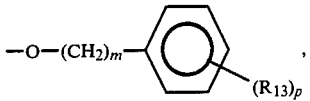

—O-lower alkyl, a 1- or 2-naphthyloxy of the formula

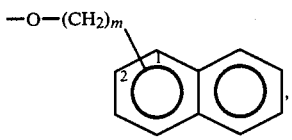

a substituted 1- or 2-naphthyloxy of the formula

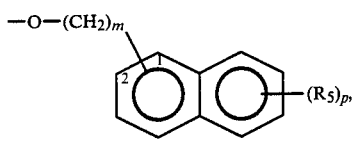

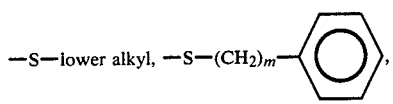

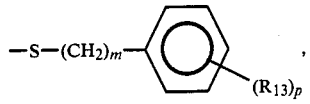

a 1- or 2-naphthylthio of the formula

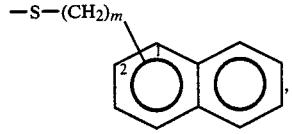

or a substituted 1- or 2-naphthylthio of the formula

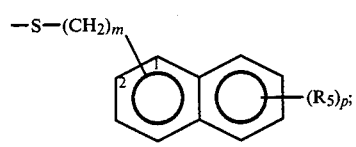

$R_9$ is lower alkyl, keto,

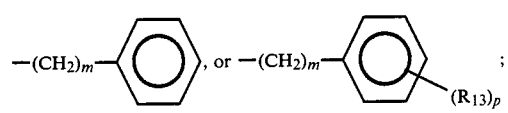

$R_{10}$ is halogen or Y—$R_{16}$;

R₁₁, R′₁₁, R₁₂ and R′₁₂ are independently selected from hydrogen and lower alkyl or R′₁₁, R₁₂ and R′₁₂ are hydrogen and R₁₁ is

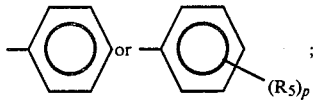

R₁₃ is lower alkyl of 1 to 4 carbons, lower alkoxy of 1 to 4 carbons, lower alkylthio of 1 to 4 carbons, chloro, bromo, fluoro, trifluoromethyl, hydroxy, phenyl, phenoxy, phenylthio, or phenylmethyl;
R₅ is lower alkyl of 1 to 4 carbons, lower alkoxy of 1 to 4 carbons, lower alkylthio of 1 to 4 carbons, chloro, bromo, fluoro, trifluoromethyl or hydroxy;
m is zero, one, two, three, or four;
p is one, two or three provided that p is more than one only if R₁₃ or R₅ is methyl, methoxy, chloro, bromo, or fluoro;
R₁₄ is hydrogen, lower alkyl,

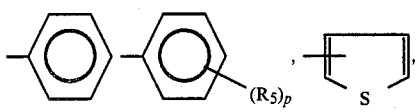

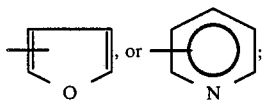

R₁₅ is hydrogen or lower alkyl of 1 to 4 carbons;
Y is oxygen or sulfur;
R₁₆ is lower alkyl of 1 to 4 carbons,

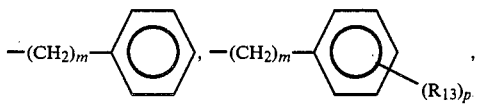

or the R₁₆ groups join to complete an unsubstituted 5- or 6-membered ring or said ring in which one or more of the carbons has a lower alkyl of 1 to 4 carbons or a di(lower alkyl of 1 to 4 carbons) substituent;
R₁₇ is lower alkyl, cycloalkyl, or phenyl;
R₁₈ is hydrogen, lower alkyl, lower alkoxy, or phenyl;
n is zero, one, or two;
R₁₉ is lower alkyl or

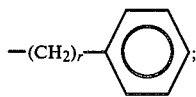

R₂₀ is hydrogen, lower alkyl,

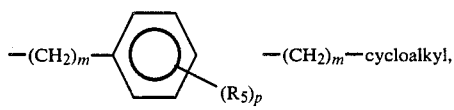

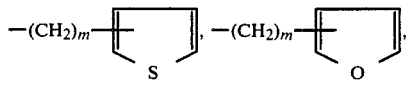

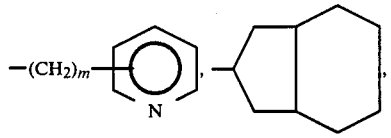

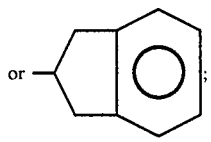

R₂₁ is hydrogen, lower alkyl

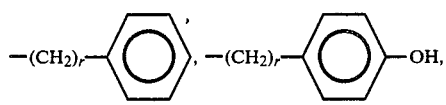

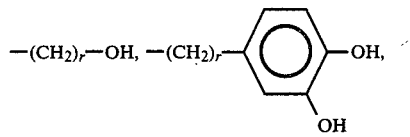

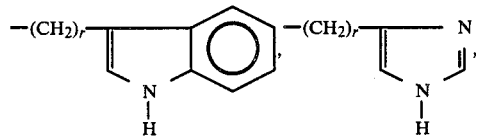

—(CH₂)ᵣ—NH₂, —(CH₂)ᵣ—SH, —(CH₂)₂—S-lower alkyl,

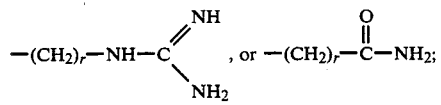

R₂₂ is lower alkyl, benzyl, or phenethyl; and
R₂₃ is hydrogen, lower alkyl, benzyl, or phenethyl.
2. A compound of claim 1 wherein:
X is

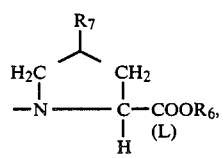

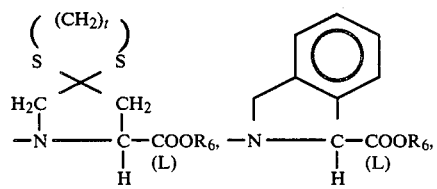

-continued

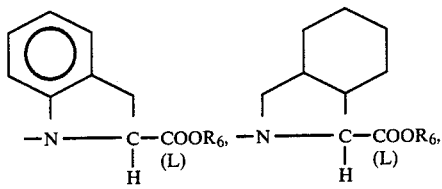

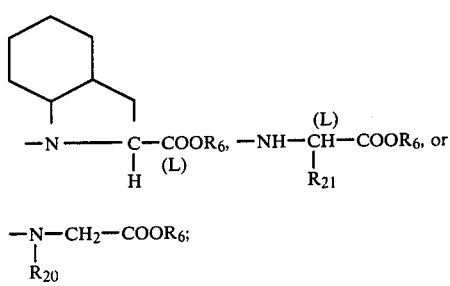

$R_7$ is hydrogen, hydroxy, chloro, fluoro, lower alkyl of 1 to 4 carbons, cyclohexyl, amino, —O-lower alkyl wherein lower alkyl is of 1 to 4 carbons, —S-lower alkyl wherein lower alkyl is of 1 to 4 carbons,

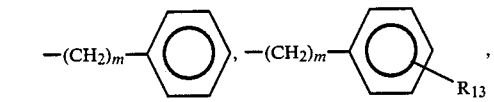

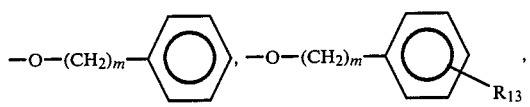

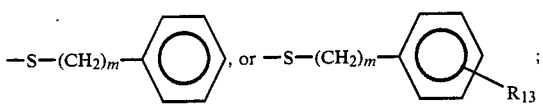

m is zero, one or two;
$R_{13}$ is methyl, methoxy, chloro, fluoro, bromo, methylthio, or hydroxy;
t is 2 or 3;
$R_{20}$ is

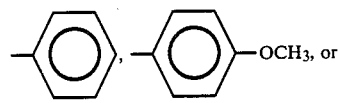

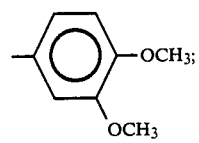

$R_{21}$ is hydrogen, straight or branched chain lower alkyl of 1 to 4 carbons,

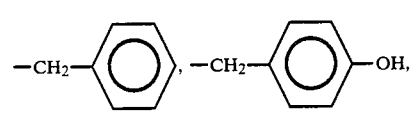

-continued

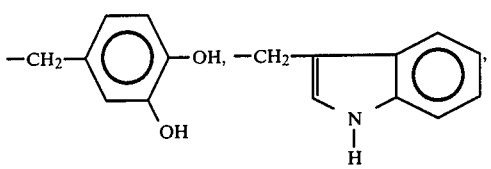

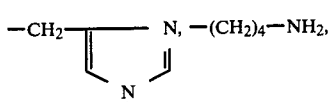

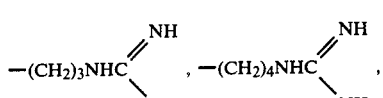

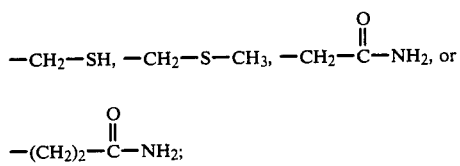

$R_6$ is hydrogen, sodium ion, potassium ion, calcium ion, lithium ion, or

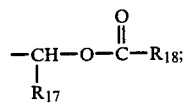

$R_{17}$ is hydrogen, straight or branched chain lower alkyl of 1 to 4 carbons, cyclohexyl, or phenyl; and
$R_{18}$ is hydrogen or straight or branched chain lower alkyl of 1 to 4 carbons.

3. A compound of claim 2 wherein:
$R_1$ is straight or branched chain lower alkyl of 1 to 4 carbons, —(CH$_2$)$_r$—NH$_2$, or

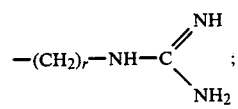

$R_2$ is straight or branched chain lower alkyl of 1 to 4 carbons,

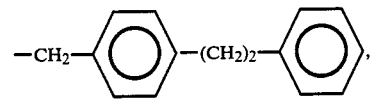

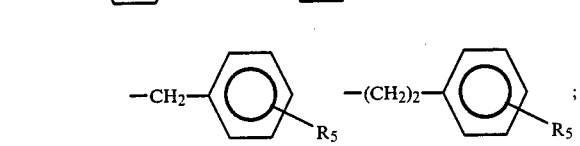

$R_3$ is hydrogen, sodium ion, potassium ion, calcium ion, lithium ion, or

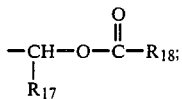

R$_4$ is straight or branched chain lower alkyl of 1 to 4 carbons,

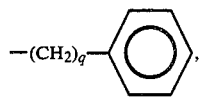

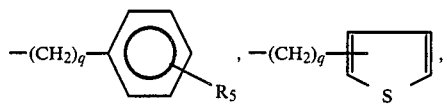

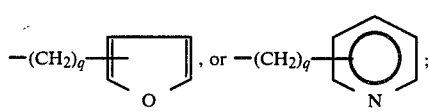

r is an integer from 3 to 5;

q is zero, one, or two;

R$_5$ is methyl, methoxy, methylthio, chloro, bromo, fluoro, or hydroxy;

R$_{17}$ is hydrogen, straight or branched chain lower alkyl of 1 to 4 carbons, cyclohexyl, or phenyl; and R$_{18}$ is hydrogen or straight or branched chain lower alkyl of 1 to 4 carbons.

4. A compound of claim 3 wherein: X is

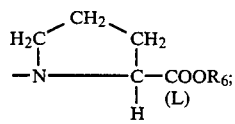

R$_6$ is hydrogen, sodium ion, potassium ion, calcium ion, or lithium ion.

5. A compound of claim 4 wherein:

R$_1$ is —(CH$_2$)$_4$—NH$_2$;

R$_2$ is methyl, n-butyl, or benzyl;

R$_3$ is hydrogen, sodium ion, potassium ion, calcium ion, or lithium ion; and

R$_4$ is n-propyl, phenyl, or 2-furanyl.

6. The compound of claim 5 wherein

R$_2$ is n-butyl;

R$_4$ is phenyl; and

R$_3$ and R$_6$ are both hydrogen.

7. The compound of claim 6, 1-[(S)-6-amino-2-[[[1-(benzoyloxy)pentyl]hydroxyphosphinyl]oxy]-1-oxohexyl]-L-proline.

8. The compound of claim 5 wherein:

R$_2$ is methyl;

R$_4$ is phenyl; and

R$_3$ and R$_6$ are both hydrogen.

9. The compound of claim 8, 1-[(S)-6-amino-2-[[[1-(benzoyloxy)ethyl]hydroxyphosphinyl]oxy]-1-oxohexyl]-L-proline.

10. The compound of claim 5 wherein:

R$_2$ is n-butyl;

R$_4$ is n-propyl; and

R$_3$ and R$_6$ are both lithium.

11. The compound of claim 10, 1-[(S)-6-amino-2-[[hydroxy[1-(1-oxobutoxy)pentyl]phosphinyl]oxy]-1-oxohexyl]-L-proline, dilithium salt.

12. The compound of claim 5 wherein:

R$_2$ is n-butyl;

R$_4$ is 2-furanyl; and

R$_3$ and R$_6$ are both lithium.

13. The compound of claim 12, 1-[(S)-6-amino-2-[[[1-[(2-furanylcarbonyl)oxy]pentyl]hydroxyphosphinyl]oxy]-1-oxohexyl]-L-proline, dilithium salt.

14. The compound of claim 5 wherein:

R$_2$ is benzyl;

R$_4$ is phenyl; and

R$_3$ and R$_6$ are both lithium.

15. The compound of claim 14, 1-[(S)-6-amino-2-[[hydroxy[1-(benzoyloxy)-2-phenylethyl]phosphinyl]oxy]-1-oxohexyl]-L-proline, dilithium salt.

16. A pharmaceutical composition useful for treating hypertension in a mammalian species comprising a pharmaceutically acceptable carrier and an anti-hypertensive compound of the formula

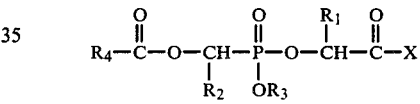

wherein R$_1$, R$_2$, R$_3$, R$_4$ and X are as defined in claim 1.

17. The method of treating hypertension in a mammalian host which comprises administering an effective amount of the composition of claim 16.

18. A pharmaceutical composition useful as an analgesic agent comprising a pharmaceutically acceptable carrier and an enkephalinase inhibiting compound of the formula

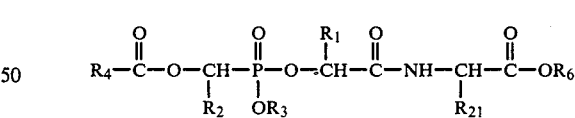

wherein R$_1$, R$_2$, R$_3$, R$_4$, R$_6$ and R$_{21}$ are as defined in claim 1.

19. The method of relieving pain in a mammalian host which comprises administering an effective amount of the composition of claim 18.

* * * * *